(12) United States Patent
Gaastra et al.

(10) Patent No.: US 12,595,493 B2
(45) Date of Patent: Apr. 7, 2026

(54) METHANATION METHOD IN A BIOREACTOR UNDER CONTINUOUS CELL-RETENTION CONDITIONS

(71) Applicant: ELECTROCHAEA GMBH, Planegg (DE)

(72) Inventors: Imko Gaastra, Planegg (DE); Manuel Hoerl, Planegg (DE); Laurent Lardon, Planegg (DE); Doris Hafenbradl, Planegg (DE); Felix Popp, Planegg (DE); Mich Hein, Planegg (DE); Hans Knudsen, Planegg (DE); Jeff Fornero, Planegg (DE)

(73) Assignee: ELECTROCHAEA GMBH, Planegg (DE)

( * ) Notice: Subject to any disclaimer, the term of this patent is extended or adjusted under 35 U.S.C. 154(b) by 785 days.

(21) Appl. No.: 17/604,743

(22) PCT Filed: Apr. 20, 2020

(86) PCT No.: PCT/EP2020/060979
§ 371 (c)(1),
(2) Date: Oct. 18, 2021

(87) PCT Pub. No.: WO2020/212621
PCT Pub. Date: Oct. 22, 2020

(65) Prior Publication Data
US 2022/0112522 A1 Apr. 14, 2022

(30) Foreign Application Priority Data
Apr. 18, 2019 (DE) ..................... 10 2019 110 387.8

(51) Int. Cl.
*C12P 5/02* (2006.01)
*C12M 1/107* (2006.01)
*C12N 1/20* (2006.01)

(52) U.S. Cl.
CPC ............. *C12P 5/023* (2013.01); *C12M 1/107* (2013.01); *C12N 1/20* (2013.01); *C12N 2500/02* (2013.01); *C12N 2500/05* (2013.01);

*C12N 2500/12* (2013.01); *C12N 2500/60* (2013.01); *C12N 2511/00* (2013.01)

(58) Field of Classification Search
None
See application file for complete search history.

(56) References Cited

U.S. PATENT DOCUMENTS

2022/0112522 A1 * 4/2022 Gaastra .................... C12N 1/20

FOREIGN PATENT DOCUMENTS

| EP | 2982740 A1 * | 2/2016 | ............ C12M 43/00 |
|---|---|---|---|
| WO | WO-2011/003081 A1 | 1/2011 | |
| WO | WO-2012/094538 A1 | 7/2012 | |
| WO | WO-2012110257 A1 * | 8/2012 | ............ C12M 21/04 |

OTHER PUBLICATIONS

Bernacchi et al., Process efficiency simulation for key process parameters in biological methanogenesis. *AIMS Bioengineering*, 1(1): 53-71 (2014).
Morocho-Jacome et al., Continuous cultivation of Arthrospira platensis using exhausted medium treated with granular activated carbon. *Journal of Hydrology*. 522(1): 467-74 (2015).
International Search Report and Written Opinion for International Application No. PCT/EP2020/060979, European Searching Authority, mailed Jul. 28, 2020.
International Preliminary Report on Patentability for International Application No. PCT/EP2020/060979, Chapter II, mailed Mar. 15, 2021.

* cited by examiner

*Primary Examiner* — Hope A Robinson
(74) *Attorney, Agent, or Firm* — RinLaures LLC; Li-Hsien RinLaures; Kristen A. Dola

(57) ABSTRACT

The present invention refers to a method to convert $H_2$ and $CO_2$ into methane by methanogenic microorganisms in a bioreactor in a continuous production process for methane enriched gas compositions, while culturing the methanogenic microorganisms under cell retention conditions and continuously removing metabolic water in the cell culture medium.

18 Claims, 8 Drawing Sheets

Fig. 14          Fig. 15

METHANATION METHOD IN A BIOREACTOR UNDER CONTINUOUS CELL-RETENTION CONDITIONS

CROSS REFERENCE TO RELATED APPLICATIONS

Figure 1:
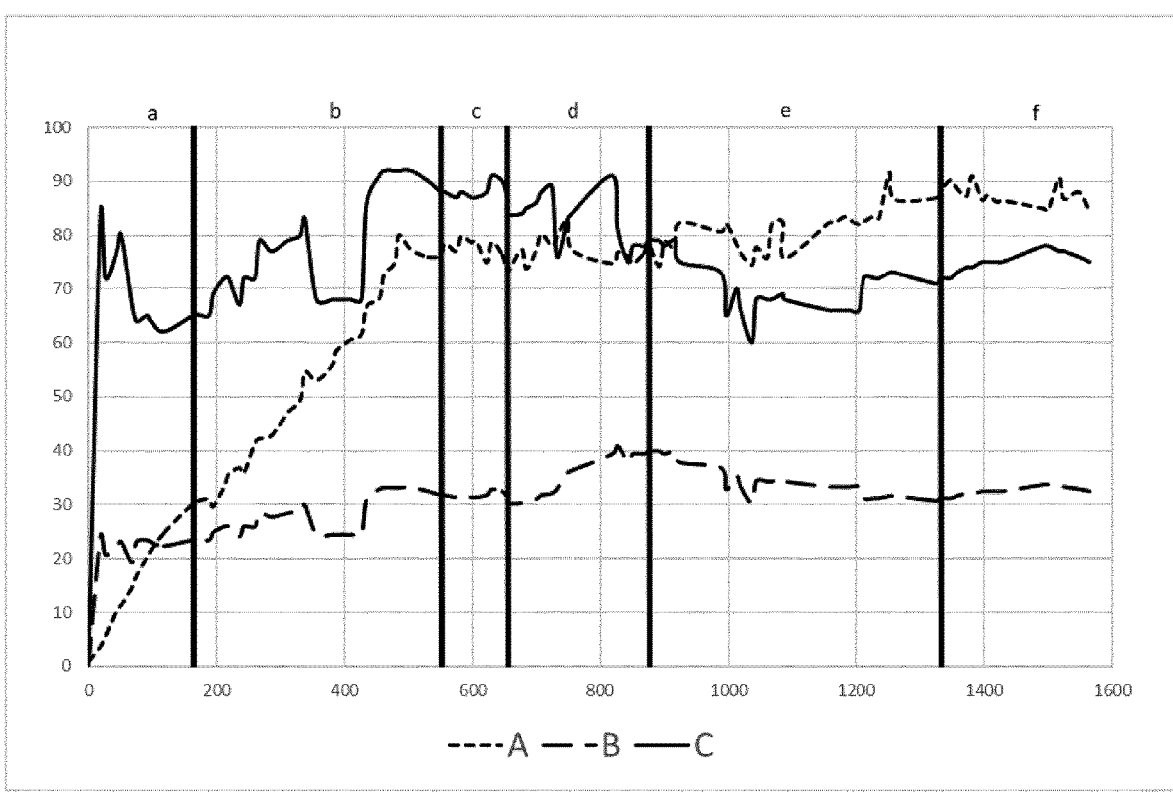

This application is the U.S. National phase of International Patent Application No. PCT/EP2020/060979, filed Apr. 20, 2020, which claims the benefit of foreign priority to German Patent Application No. DE-10 219 110 387.8, filed Apr. 18, 2019, each of which is herein incorporated by reference in its entirety.

The present invention refers to a highly efficient method for producing biogenic methane using $H_2$ and $CO_2$ by methanogenic microorganisms in a bioreactor even under conditions of reduced nitrogen supply in the methane production phase.

Methane has the highest energy density per carbon atom among fossil fuels and its potential for energy conversion is far greater than any other natural gas, obtained directly by combustion in presence of oxygen or using fuel cells to produce electricity. Methane's potential for energy generation has become increasingly relevant in the global market.

As natural gas, therefore, methane constitutes a sustainable and renewable energy source and already today increasingly substitutes coal and other fossil fuels.

Recent research has therefore focused on the development and improvement of methods for producing methane with methanogens, e.g. Archaea, which are capable of producing methane from carbon dioxide and hydrogen very efficiently. Presently, the state of the art describes several attempts to enrich gas compositions with methane produced by employing methanogenic microorganisms. For industrial production of methane using Archaea, e.g., *Methanothermobacter thermautotrophicus* strain UC 120910 (ECH100 or ECH0100).—deposited and commercially available may regularly be used.

Upgrading biomethane production to an established scalable and reliable renewable energy source proves to remain a challenge, especially owing to the requirement for a continuous process.

Within a bioreactor, a culture of hydrogen using methanogenic microorganisms catalyses the methanation reaction as follows:

$$CO_2 + 4H_2 \rightarrow CH_4 + 2H_2O \qquad \text{(equation 1)}$$

The water produced by this methanation process (see equation 1), which is also called "metabolic water" or "free water" has to be continuously discharged during the methanation process in a sewage system to to maintain a constant liquid level in the bioreactor and to prevent overflowing of the bioreactor due to the increase in the liquid volume. Thus, with this discharged water, also medium components like minerals/nutrients (salts, ions, micronutrients) important for maintaining the methanogenic microorganisms and to allow for effective methanation are lost. Another problem associated with the production of metabolic water is the dilution of the medium components within the culture medium. Since the methanogenic organisms require a constant medium concentration to grow and maintain themselves, concentrated medium stock solutions in the prior art have to be laboriously added continuously to guarantee a normal methanation rate. This continuous addition of fresh medium stock is a significant detrimental part of the operational costs of the process.

One way to eliminate medium loss is to recover and reuse the chemical components from the diluted discharge water. In general, medium recovery systems for biotechnological processes are insufficiently researched. For example, for the production/harvesting of *Arthrospira platensis* (*A. platensis*) a filamentous, gram-negative cyanobacterium, a medium recovery strategy is known (Morocho-Jácome et al., 2015). This strategy consists of a complex cascade of different filters, removing *A. platensis* from the culture medium and reusing the original cell-free culture medium. However, *A. platensis* produces no metabolic water and thus does not dilute its growth medium. Therefore, concentrating the minerals in the discharge water is not required in this prior art.

Several techniques exist to remove excess water. A well-known technique is distillation, which would allow to remove excess water by evaporation. A more recent technique to remove water is Reverse Osmosis (RO). With RO, the dissolved compounds can be removed from water by using high pressure and nano-sized membranes.

It is thus an object of the present invention to overcome the described disadvantages of the state of the art, especially to provide a scalable, reliable and continuous production process for methane enriched gas compositions.

The object of the present application has been solved by the newly developed method as specified in the present invention.

In particular, to achieve the stated aim a method to convert $H_2$ and $CO_2$ into methane by methanogenic microorganisms in a bioreactor in the methane production phase is provided, comprising the steps:

i. culturing the methanogenic microorganisms in a suitable liquid culture medium comprising minerals in a continuous process;

ii. culturing the methanogenic microorganisms under cell retention conditions;

iii. contacting the methanogenic microorganisms with at least one feeding gas comprising $CO_2$ and $H_2$;

iv. continuously removing metabolic water in the culture medium from the bioreactor;

v. collecting methane or a methane enriched gas composition.

The method of the present invention does comprise a step of culturing methanogenic archaea, which is based on typical culture conditions for archaea, which have been previously described and which are known to the practitioner. Such conditions are influenced and controlled—according to the skills of a practitioner by common parameters affecting the culture including temperature, pressure, volume, humidity, salt content, conductivity, carbon content, nitrogen content, vitamin content, amino acid content, mineral content, or any combination thereof.

According to the present invention, the step of culturing the methanogenic microorganism in the method to produce methane from $CO_2$ and $H_2$ containing gas or gases in a bioreactor comprises: keeping said methanogenic microorganism in a suitable liquid culture medium providing suitable minerals or nutrients such as e.g. a nitrogen source and salts.

$CO_2$ and $H_2$ may be e.g. applied as pure gases. $CO_2$ may be also or alternatively delivered using the supply of industrial gases. Such industrial gases depending on their source may comprise very different gas compositions. They have primarily in common that they contain a relatively high amount of $CO_2$ in comparison to air. They may contain a normal (air-like) partial amount of oxygen and/or nitrogen, however depending on their origin they may also be oxygen free. Additionally, they may contain substantial amounts of at least one of the following, particularly carbon monoxide, hydrogen and hydrogen sulfide, other sulphur compounds (sulfides, disulfides, thiols), siloxanes (organic silicon compounds), halogenated compounds, ammonia, and organo-chlorines, i.e. pesticides and other synthetic organic compounds with chlorinated aromatic molecules.

Without the newly suggested cell retention step according to the invention or i.e. in classical culturing methods of the prior art quite number of cells are continuously washed out of the bioreactor and these cells have to be replaced by further cycles of cell division and cell growth therefore by utilization of $CO_2$ and $H_2$ for the generation and growth of cells rather than for the generation of the aimed methane output, which is unfavourable for the efficiency of the system. Alternatively, and/or additionally there may be the option to supply a sufficient amount of new methanogenic microorganisms to compensate the amount washed out.

The inventors of the present invention have advantageously and surprisingly found by running a bioreactor under cell retention condition that this condition increases the overall efficiency of the system as the feeding with $CO_2$ and $H_2$ is essentially used for methane production. The efficacy of the system was observed to be 30% or higher or preferably to be 50% or higher than in comparable experiments where no cell retention conditions were applied. Processes, which are included in the calculation of this efficacy are the reduction of costs, saving of nutrients while increasing the overall methanation rate.

According to the present invention a "phase" in the sense of the invention describes a condition or state of the methanogenic microorganisms in the bioreactor of the invention, which is characterized by specific fermentation conditions, which are applied to the methanogenic microorganism, e.g., the ratio of the partial pressures of hydrogen and carbon dioxide or a specific value or range of at least one nutrient, which is applied, e.g. ammonium and/or the settings of the bioreactor to keep cells in the reactor (cell retention) or not.

A "cell growth phase" according to the present invention is a phase mainly characterized by an increase of the biomass of the methanogenic microorganisms by cell division and cell growth. A "methane production phase" according to the present invention is a phase mainly characterized by methane production rather than cell division and cell growth. However, during any cell growth phase, the cells may also or may not produce methane and during any methane production phase, the overall biomass may also increase.

According to the present invention the term "cell retention conditions" refers to conditions in a running bioreactor, which enable and guarantee that cells, i.e. the methanogenic microorganisms are kept inside the bioreactor or are recycled and reintroduced into the bioreactor. Many ways to enable such cell retention conditions in a running bioreactor in a continuous process are possible and easily accessible for a skilled person.

The growth phase and/or the methanation production phase may be performed via culturing the cells under cell retention conditions. It is also possible that a phase under cell retention conditions according to the present invention is flanked alternatively one side or both sides by a growth phase ora methanation production phase performed via culturing the cells under no cell retention conditions. By "culturing the cells under no cell retention conditions" according to the present invention is meant a situation in a running bioreactor, which does not enable and does not guarantee that cells, i.e. the methanogenic microorganisms are kept inside the bioreactor, i.e. methanogenic microorganisms will be washed out of the bioreactor during this phase.

In the context of the present application, methanation, or methanogenesis or biomethanation, is understood as the production of methane or a methane enriched gas composition as carried out by methanogenic microorganisms, such as those included in a list of methanogenic microorganisms suitable to carry out the present invention as described below.

In particular, the methanation reaction, as previously known and as suitable according to the present invention, consumes $H_2$ and $CO_2$ at a stoichiometry of 4:1 (see above, equation 1).

According to the present invention, methanogenic microorganisms are cultured in a bioreactor in order to produce biomethane. Such methanogenic microorganisms, or autotrophic methanogenic microorganisms may be anaerobic archaea or even recently classified aerotolerant archaea, either in pure strains, or in consortia with a plurality of, i.e. two or more, strains, or in mixed cultures wherein methanation may be also encouraged by syntrophic exchange across different species.

In the understanding of the present invention, a "bioreactor" stands for a reactor, and is either a bioreaction vessel, or a bioreaction enclosure, or a bioreaction tank, and/or at least a bioreaction chamber, and/or a cell, or a combination thereof, as also intended in the state of the art, able to withstand variations of e.g. temperature and/or pressure, among others, and/or able to maintain whichever imparted values of e.g. temperature, and/or pressure are assigned or have to be maintained, before, after or during the reaction process, and wherein the intended reactions relevant for carrying out the invention may take place. Such reactions are understood as bioreactions as they pertain to the domain of reactions wherein microorganisms are involved, and herein referring to their normal physiology—such as e.g. metabolic fermentation, or aerobic or anaerobic digestion—and that, as such, require suitable environments, suitable cultures of microorganisms, suitable culture mediums and suitable reactants to occur. A bioreactor in the meaning of the invention, performs reliably within the tolerance values of each variable in order to enable the method as disclosed, and it is expected to allow the listed steps to be carried out reliably over time.

A suitable reactor for culturing methanogenic microorganisms, may be, by means of example only, a shake tank bioreactor, a continuous stirred tank bioreactor, an intermittent stirred tank bioreactor, a hollow fiber membrane bioreactor, a bubble column bioreactor, an internal-loop airlift bioreactor, an external-loop airlift bioreactor, a fluidized bed bioreactors, a packed bed bioreactor, a photo-bioreactor, a trickle bed reactor, a microbial electrolysis cell, etc., and/or combinations thereof.

The operation mode of a bioreactor is classified as batch processes, fed-batch processes and continuous processes. According to the different embodiments of the method herein presented, a reactor may be chosen that most closely addresses the specific dynamics of a culture or the convenience by which methane is hereby extracted. In an embodiment of the present invention, a bubble column reactor, or a variant of it, such as an airlift bioreactor, or a continuously stirred tank reactor, and/or any of the above, may be used to conveniently carry out the method as described and a continuous culture is preferred, wherein near-balanced growth, with little fluctuation of nutrients, metabolites, cell number and biomass are observed.

According to the present invention, the method herein disclosed is concerned with the culturing of methanogenic microorganisms in a "continuous process", wherein such continuity is understood as continuity in the production of methane and continuity in the culture, wherein no step of separating inactive terminal biomass from active members of the colony is required. It is instead encouraged that dead biomaterial is kept in the reactor together with the active members across several stages of growth, as it is found advantageous that said biomass or biomaterial provide further substrate for the active culture, intensifying nutrition availability. In the understanding of such continuity of methane production and culture, is also included the understanding that a continuous supply of suitable reactants (e.g. feeding gases, etc.) is given to the culture, allowing it to carry out its methane production task without significant alteration of the measured amount of produced methane (i.e. yield of methane) obtained from any cycle of methanogenic activity across the culture and within the operational phases of the reactor.

Ensuring a continuous methane production is a relevant feature of the present invention and an advantageous effect of implementing the steps of the method as described. According to the invention, methane is produced by methanogenic archaea from single strains or in mixed cultures, wherein a mixed culture is either a culture where a plurality of, therefore two or more, strains may also be employed, or a culture where a plurality of additional species interact with methanogenic archaea, or any combination thereof.

Furthermore, it is an advantageous step of the method according to the present invention to remove, regularly or continually, excess moisture and/or an excess of metabolic or so-called free water from the culture media thereby ensuring the correct dilution and/or dispersion of the nutrients in the media. "Metabolic water" according to the present invention refers to water or $H_2O$ molecules, which are produced by the methanogenic organisms during metabolic activity and the process of methanogenesis, i.e. mainly in the methane production phase.

According to an alternative embodiment of the method of the present invention in step iv. the removing of the metabolic water in the culture medium from the bioreactor is done discontinuously at certain time points instead of doing it continuously.

According to an additional embodiment of the method of the present invention step i. comprises at least one cycle of culturing the methanogenic microorganisms under:

a first phase in a continuous process in a suitable liquid minerals containing culture medium comprising a reduced supply of at least one mineral; followed by a second phase, characterized by refreshing the culture medium;

optional followed by a third phase in a continuous process comprising a reduced supply of at least one mineral.

A "at least one mineral" according to the present condition within the first phase and/or third phase refers to typical minerals, which are present in classical cell culture mediums, e.g. a nitrogen source and/or salts. According to one embodiment the "at least one mineral" is a nitrogen source. According to another embodiment the "at least one mineral" is a salt, e.g. a chloride containing salt. The chloride can be present in the salt respectively dissolved as saline solution as the anion of NaCl, MgCl, KCl, $NH_4Cl$ or any other suitable chloride salt known to the skilled person. The "at least one mineral" which supply is decreased may be the same or be a different one in the first and the third phase. A "refreshing of the culture medium" according to the present invention within the second phase can be realized by changing the cell culture medium at least partly or by adding at least one nutrient, which triggers cell division and cell growth. Nutrients, which trigger cell growth and cell division are well known by an artisan and include the addition or the increase of a nitrogen source, a sulfur source, phosphorous and cell growth factors. A combination of the described options for refreshing of the culture medium is also a possible option according to the present invention. This second phase can optionally be followed by a third phase, wherein the cells are again cultured in a continuous process comprising a reduced supply of at least one mineral. Then, the second phase is a transition phase flanked between two phases in a continuous process within the at least one cycle. Such a "refreshing of the culture medium" may be but not necessarily be applied every month, every half year for at least one day or at least one day to five days or at least one day to four days at least one day to three days.

According to an embodiment of the present invention additional nutrients are supplied to the cell culture medium continuously depending on the need of the cultured cells and the consumption of nutrients by the cells in a continuous process.

According to another embodiment of the method of the present invention step ii. comprises at least one cycle of culturing the methanogenic microorganisms under:

a fourth phase under cell retention conditions; followed by a fifth phase, characterized by culturing the cells under no cell retention conditions;

optional followed by a sixth phase under cell retention conditions.

A "culturing the cells under no cell retention conditions" according to the present invention within the fifth phase refers to conditions in a running bioreactor, which does not enable and does not guarantee that cells, i.e. the methanogenic microorganisms are kept inside the bioreactor, i.e. methanogenic microorganisms will be washed out of the bioreactor during this phase. This fifth phase can optionally be followed by a sixth phase, wherein the cells are again cultured under cell retention conditions. Then, the fifth phase is a transition phase between two phases under cell retention conditions within the at least one cycle.

The inventors of the present invention have found, that culturing the methanogenic microorganisms under such no cell retention conditions may be advantageous at a certain running time of the reactor. This phase under such no cell retention conditions may promote cell division and cell growth, which may have a positive effect on the overall methanation process efficiency. Such no retention conditions may be but not necessarily be applied every month, every half year for at least one day or at least one day to five days or at least one day to four days at least one day to three days.

According to another embodiment of the present invention within the method the step of culturing the methanogenic organisms comprises:

controlling and reducing the supply of a nitrogen source in the methane production phase to receive a nitrogen source concentration in the culture medium in an amount of 0.2 mol/L/day to 0 mol/L/day or of 0.02 mol/L/day to 0.005 mol/L/day preferably between 0.11 mol/L/day 0.005 mol/L/day.

Methanogenic microorganisms generally need a nitrogen source and accordingly all published prior art documents the supply of nitrogen in one or the other way. Nevertheless, the inventors of the present invention have surprisingly found, that by cultivating methanogenic microorganisms under cell retention conditions according to the present invention it is possible to tremendously reduce or even completely stop the supply of the nitrogen source in the methane production phase and still enable a high and quite stabilized methanation rate while observing a stabilized maintained cell culture number. Optional it is possible to have a growth phase before culturing the cells in a phase of culturing the cells under cell retention conditions, where a sufficiently large population of microorganisms is established before the methanation process is pronounced and cell retention conditions applied. Optional and differently is also to have a phase of culturing the cells under cell retention conditions flanked by two other phases, e.g. two cell growth phases under no cell retention conditions. It is believed—without being bound by that theory—that when all methanogenic microorganisms are kept inside the reactor, growth of the cells is only required in a pronounced amount in the "growth phase" at the beginning of the start-up of a reactor and not during methane production phase, resulting in a nitrogen savings for the cells during the methane production phase. However, if a cell population of sufficient number is directly applied in the start-up of the reactor a growth phase is not necessary.

Additionally, it is believed—without being bound by theory—that the reason why the total cell number of the methanogenic microorganisms stays stabilized over time even under prolonged reduction or even stop of the external supply of the nitrogen source in the methane production phase, is that the nitrogen during natural turn-over of pre-existing cell mass of the methanogenic microorganisms developed in the growth phase is used to build up new cells during the archaea generation cycle in the methane production phase. This would mean that the nutrients of e.g. dying methanogenic microorganisms including nitrogen are recycled by the living methanogenic microorganisms to grow and/or to build up new cells by division.

The present invention is besides others characterized by a step of controlling the external supply of the nitrogen source and/or the (resulted) concentration of the nitrogen source (i.e. ammonia) within the cell culture medium. In this context, controlling is understood in the general common meaning of keeping under constant monitoring the parameters related to the culture and essentially measuring said parameters or status indicators, using common methodologies and measuring instrumentation known in the art, since it might not be sufficient to keep under constant monitoring and therefore only control this parameter of the culture; therefore a further embodiment of the present invention comprises in particular regulating the nitrogen source concentration within the cell culture medium continuously. In the understanding of the present application, regulating is intended as actively maintaining a "given value" or a given value span for a parameter, e.g. the nitrogen source concentration of the culture, by using appropriate means to do so.

A "given value" according to the invention may be a defined value with given tolerances, tolerances within the measurements system or tolerances due to the variability within the culture or due to the culture diversity, wherein said value is suitable for enabling methanation; or a given value may be a range of suitable values, which achieve the same effect on methanation as a given value.

Furthermore, common culture or growth mediums to be provided to the culture of methanogenic organisms may include common inorganic elements, in their elemental forms or in any suitable non-toxic salts thereof, e.g. sodium, potassium, magnesium, calcium, iron, chloride, sources of sulfur, e.g. hydrogen sulfide or elemental sulfur, phosphorus sources, e.g. phosphate, nitrogen sources, e.g. ammonium, nitrate or nitrogen gas. Typical salts utilized for culturing methanogenic organisms according to the present invention are NaCl, $KH_2PO_4$, FeCl2-$4H_2O$, $Na_2SeO_3$, $Na_2S$, $NH_4OH$ and $MgCl_2$.

According to another embodiment of the present invention the step of culturing the methanogenic organisms further comprise:
    providing a sulfide source, preferably in the form of $Na_2S$ in the culture medium;
    keeping the culture conditions anaerobic or facultatively anaerobic;
    optionally stirring the culture;
    keeping the temperatures in a range from 32° C. and 85° C.

According to the present invention, the step of culturing the methanogenic microorganism in the method to produce methane from industrial gases containing $CO_2$ in a bioreactor further comprises: providing a sulfide source, preferably in the form of $Na_2S$ in the culture medium; keeping the culture conditions facultatively anaerobic and/or anaerobic; optionally stirring the culture, wherein the stirring of the culture can be carried out regularly, in intervals, continuously, or keeping the soluble culture at least in a certain slow and constant movement; removing metabolic water from the culture continuously; and keeping the temperatures in a range between 32° C. and 80° C.; preferably 50-70° C. or around 62° C.

While the temperatures may vary according to the presence of selected microorganism species within the culture, each of which better thrive within set ranges of temperatures, for most of the methanogenic microorganisms increased temperatures are not detrimental, and they may even assist in optimizing cellular metabolism and thus metabolic turnover or even methanation. In an industrial process a temperature must be controlled by energetic regulation; in this regard it is to be considered a valuable feature to reduce energy expenditure by enabling temperature control.

Consequently, it is of substantial importance to balance the optimized culture temperature and the corresponding hydrogen solubility against the costs for energy input. Interestingly, the method of the present invention was found to be most efficient in a temperature range between 32° C. and 85° C., or alternatively 50 to 70° C. or further alternatively around 62° C. at atmospheric pressure. If according to some embodiments one or more steps of the method according to the invention are carried out in a pressurized atmosphere, then the pressure is chosen to be preferably up to 16 bar, alternatively up to 20 bar, alternatively up to 50 bar, alternatively up to 68 bar, alternatively up to 110 bar or even up to 420 bar.

For other temperature or pressure ranges hydrogen solubility can be used as comparative feature. Accordingly, the present invention also refers to a culturing process at pressures equal or between the range of 1 to 10 bar. High pressure, e.g. 16 bar, 20 bar, 35 bar, 40 bar or 60 bar and correspondingly, higher temperatures, which would allow the same hydrogen solubility as at a temperature range between 32° C. and 85° C., or alternatively 50 to 70° C. or further alternatively around 62° C. at atmospheric pressure are also encompassed.

Methanogenic microorganisms, in general, may live and grow also in a plurality of other and even extreme temperature ranges up to and well above 100° C., e.g. 140° C.;

accordingly, the above temperature range is an indication of a preferred range, but it is not to be understood as limiting the scope of the invention.

According to another embodiment of the present invention the culturing of the methanogenic organisms comprises a cell growth phase prior to the methane production phase, comprising the steps of:

controlling and regulating the concentration of a nitrogen source within the culture medium in a range of 0.2 moL/L/day to 0.005 moL/L/day, preferably of 0.02 moL/L/day to 0.01 moL/L/day to enable cell division and cell growth of the methanogenic microorganisms;

culturing the methanogenic microorganisms up to a density in the culture medium measured as $OD_{610}$ being at least 1,9 up to 200 or at least 20 up to 120, preferably at least 60 up to 100 and corresponding to a dry weight of the microorganisms in the culture of at least 0.5 g/L and up to 50 g/L or at least 6.5 g/L and up to 31.3 g/L or at least 18.3 g/L and up to 26.1 g/L respectively.

The $OD_{610}$ (optical density at 610 nm) or briefly optical density of microorganisms in a culture is a viable parameter to measure the cell count or concentration at each time point. A straightforward relationship between a given cell count and the efficiency of the microorganisms in a culture it does not appear to have been universally established, nevertheless in the understanding of the results of the method according to the present invention, a high density culture produces advantageous results in terms of methane production and yield.

In particular the optical density (OD) of the culture according to the present invention is measured utilizing common methods and standards known in the art. Optical density, or, rather, turbidity measurements as a form of cell counting are performed using a spectrophotometer, is typically operated around or at 600 nm, but accordingly other wavelengths may be suitable.

Because the optical density may vary according to the measurement setup, it is often useful to indicate the dry weight or biomass density of the microorganisms in the culture as a measure of the amount of cells present in a culture at a given time point or growth phase. It is possible to establish a correlation between measurements of OD of a given culture at a given growth stage and dry weight by building a curve of a number of different OD values of the culture obtained at different concentrations and measuring the dry weight of the dried sample of culture accordingly, using standard methods known in the art. This will provide a set of data point of dry weight as a function of the optical density; the slope of the regression line of such data set usually defines the correlation between dry weight and optical density. According to the inventors, in the present application a value of $OD_{610=4}$ translates, roughly, into a biomass density of 1 g/L.

According to the invention the culture of the methanogenic microorganisms can be guided or led into a high density culture with an $OD_{610}$ of at least 14, but preferably above 20, further also above 30, further above 40 and even up to 120 or 200 by supplying sufficient nutrient to the culture and simultaneously removing free or metabolic water from the culture. The method of the present invention can thus be suitably performed in culture of one or more strains of methanogenic microorganism, having throughout the various developmental stages a measurable $OD_{610}$ between 60-200; further an $OD_{610}$ between 14-120; further an $OD_{610}$ between 20-120; further an $OD_{610}$ between 30-120; further an $OD_{610}$ between 40-120; further an $OD_{610}$ between 50-120; further an $OD_{610}$ between 50-100; further an $OD_{610}$ between 14-80; further an $OD_{610}$ between 20-80; further an $OD_{610}$ between 30-80; further an $OD_{610}$ between 40-80; further an $OD_{610}$ between 20-80; further an $OD_{610}$ between 30-40; further an $OD_{610}$ between 40-60; further an $OD_{610}$ between 20-40.

A high optical density corresponding to a high number of cells is obtained into the growth phase and maintained by keeping the members of the culture in the bioreactor across the entire stages of their lives to their terminal stage, so that the remains of the inactive cellular bodies may provide nutrients to the active members of the culture.

Preferably, according to a further embodiment of the invention the nitrogen source is but not limited to ammonium compounds, preferably in the form of $NH_4OH$ or $NH_4Cl$ or combinations of the aforementioned. According to an embodiment the nitrogen source is an ammonium compound, preferably in the form of $NH_4OH$.

According to one embodiment of the present invention the method further comprises the step of setting an initial pH value to be at a given value of below pH 9, below pH 8 or at pH 7 and subsequent continuously controlling the pH value.

According to an embodiment the inventors of the present invention have surprisingly found that after setting an initial pH to be at a given value, this pH value can be maintained over the whole experimentations throughout the various conditions of the present invention. Unexpectedly was that even after running the bioreactor under successive phases of reduction (up to 440 h) and complete stopping of the supply of the nitrogen source (up to 216 h), e.g. concretely in the form of NH4OH without adding further amounts of a base as surrogate for the missing basic OH moiety of the NH4OH compound, this does not require an additional supply of a base (and/or acid) to maintain the pH at a given value. Thus, providing the advantage to reduce the process cost for running the bioreactor as the supply of the nitrogen source are reduced while saving time and costs to continuously control and regulate the pH at a given value.

According to an embodiment of the present invention the pH is optionally continuously controlled and/or alternatively further regulated, i.e. stabilized to be kept at a given different value.

According to an embodiment of the present invention the step of controlling and regulating the pH value continuously to be kept at a given different value is done by dosing suitable amounts of a base and/or an acid, e.g. $NaOH/HCl$ or $NH_4OH/HCl$ to the culture.

According to another embodiment of the present invention the removing of the metabolic water comprises the step of filtrating excess water away from the culture medium and/or comprises the step of evaporating excess water from the culture medium. One not limiting way how this can be performed is disclosed in Examples 1-3.

The means how to evaporate excess water from the culture medium in a running bioreactor is well known by a skilled person. One not limiting way how this can be performed is disclosed in industrial scale—see Example 5.

According to one embodiment the step of filtrating excess water away from the culture medium is performed by reverse osmosis using at least one semipermeable membrane for water in contact with the culture medium. The technique and how to perform reverse osmosis are well known to the skilled person. One not limiting way how this can be performed is disclosed in industrial scale—see Example 4.

Separating the excess (metabolic) water from the aqueous cell culture medium by filtration, e.g. reverse osmosis results in a concentrated and recovered cell culture medium. Advantageously, the at least one membrane semi-permeable for water in contact with the culture medium is located in the proximity of a device, e.g. a tube with is in contact with the culture medium and is under a negative pressure resulting in a net efflux of water from the bioreactor. Using ultrafiltration according to the present invention, all cells are kept inside the reactor (cell retention) and only the excess water is removed from the soluble components of the cell culture medium.

Reusing this recovered medium will lower the amount of fresh medium stock required to run the bioreactor. Besides the cost motivation, there might also be a motivation from a legislative perspective to reuse the minerals in the excess water phase, since it might contain compounds at concentrations exceeding the limits set by the local authorities for discharge into wastewater treatment plants.

According to an embodiment of the present invention the step of filtrating excess water away comprises the step of:

removing fractions of cell-free culture medium from the bioreactor by filtration through at least one porous membrane in contact with the culture medium, preferably having a pore size of 0.4 to 0.1 μm, particularly preferably of 0.3 μm; and optionally, subsequently concentrating the minerals from the removed culture medium preferably by at least one further filtration step, e.g. nanofiltration, ultrafiltration and/or by at least one distillation step; and optionally, at least partially recycling the concentrated minerals back to the bioreactor.

Using filtration means of appropriate pore-diameter all cells are kept inside the reactor (cell retention) and only the produced process water with the soluble components of the cell culture medium (cell-free fractions of cell culture medium) are removed from the bioreactor. The porous membrane in contact with the culture medium suitable for microfiltration may be located anywhere in the bioreactor as long as a continuous flow of the removed fractions of cell-free culture medium is possible. The membrane can e.g. be located close to the surface of the cell culture medium in the direction of the top of the bioreactor or be directed close to or at the bottom of the bioreactor. An example is depicted in FIG. 14. Here, a laboratory scale reactor was supplied with H₂, generated by an electrolyser, and CO₂. The flow rates of hydrogen and carbon dioxide were adjusted typically to a 4:1 ratio. The produced metabolic water of the reactor was removed with a ceramic filter, which was located inside the reactor. With this membrane the complete metabolic water containing dissolved nutrients was removed, only cells were retained in the reactor. To balance the loss of nutrients, media stock solutions were dosed according to the discharge volume.

According to an embodiment of the present invention all minerals of the formerly removed fractions of cell-free culture medium are fully recovered and the concentrated minerals are recycled back to the bioreactor.

According to another embodiment of the present invention all minerals of the formerly removed fractions of cell-free culture medium are at least partially recovered and the concentrated minerals are recycled back to the bioreactor. Non-limiting examples of at least partially or fully recovered minerals are Nickel, Cobalt, Iron, Potassium, or Phosphorus.

According to an embodiment of the present invention the porous membrane is made of ceramic material, polyethylene or stainless steel.

In an alternative embodiment, also cells may be at least partly and only time-wise removed from the bioreactor and returned to the reactor after passing an appropriate porous membrane.

According to an embodiment of the present invention the method further comprises the step of controlling and optionally regulating the concentration of at least one entity of the minerals in the culture medium by additional adding of minerals. To balance the loss of nutrients, e.g. media stock solutions can be dosed according to the discharge volume.

The step of additional adding to the culture minerals or nutrients may be performed in a continuous or a discontinuous mode and includes minerals as e.g. Sodium, Tungsten, Molybdenum or Selenium. This step of additional adding to the culture minerals or nutrients is not to be understood as limiting the present invention but should be considered as helpful to the practitioner. Methanogenic microorganism, in general, may live and grow also in the presence of multiple minerals or nutrients.

Autotrophic methanogenic microorganisms are herein intended as microorganisms which derive nutrition from inorganic reactions with their surrounding environment, e.g. by reducing carbon dioxide, to perform biosynthesis of methane. An example of autotrophic microorganisms is given by hydrogenotrophic microorganisms, which derive their nutrition from utilizing hydrogen; in particular, hydrogenotrophic methanogenic microorganisms are able to convert hydrogen and carbon dioxide into methane as part of their metabolic processes. The role of methanogenic microorganisms in the ecosystem is unique as it helps removing excess carbon dioxide and fermentation products in the final stage of decay of organic matter. In absence of methanogenesis large amounts of carbon bound to compounds from decaying matter would accumulate in anaerobic environments.

According to an embodiment of the present invention the at least one methanogenic microorganism is selected from the group of Archaea or archaebacteria comprising of *Methanobacterium, Methanobrevibacter, Methanothermobacter, Methanococcus, Methanosarcina, Methanopyrus* or mixtures thereof.

According to an embodiment of the present invention, wherein within the methane production phase under cell retention conditions at least 60% and preferably more than 80% of the overall methanogenic microorganisms in the bioreactor have a ratio of length to width of 5:1 to 3:1, preferably from 4:1 to 3:1, particularly preferably 3:1.

Figure 17:
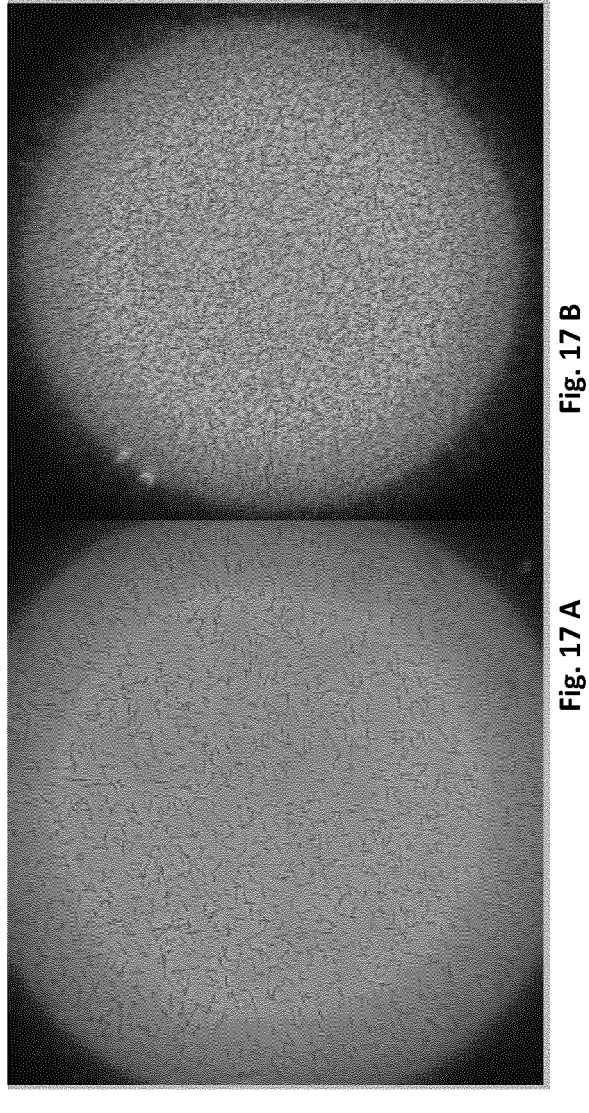

According to the experimentation the inventors performed especially the test methanogenic microorganism Methanothermobacter thermautrophicus UC 120910 (ECH0100) showed such remarkably change in cell morphology during the various phases under cell retention conditions towards comparable conditions under no-cell retention conditions (see FIG. 17 A, B). There are preliminary hints that these morphology changes are reversible (data not shown). Without being bound by theory there are indications that the observed changes in cell morphology under cell retention conditions towards comparable conditions under no-cell retention conditions as stated above can be also observed in other methanogenic microorganisms claimed following culturing these methanogenic microorganisms under cell retention conditions.

REFERENCES

Morocho-Jácome, A., Mascioli, G., Sato, S., & Monteiro de Carvalho, J. (2015). Continuous cultivation of

*Arthrospira platensis* using exhausted medium treated with granular activated carbon. Journal of Hydrology, 522(1), 467-474.

SHORT DESCRIPTION OF THE FIGURES

FIG. 1: Filtrating excess metabolic water away by using porous membrane filter under cell retention conditions and regulating the pH under ammonium reduction conditions (preliminary experimentation, cell retention experiment 1). Phases/conditions (horizontal coordinate): run time [h]. Vertical coordinate: A: OD610. B: WD [L/L/d]. C: Conversion [%]. Phases/conditions: a: cell growth. b: cell retention (filter testing). c: methane production under no cell retention. d: production under cell retention. e: methane production under cell retention and ammonia reduction. f: methane production with cell retention without ammonia feeding.

Figure 2:
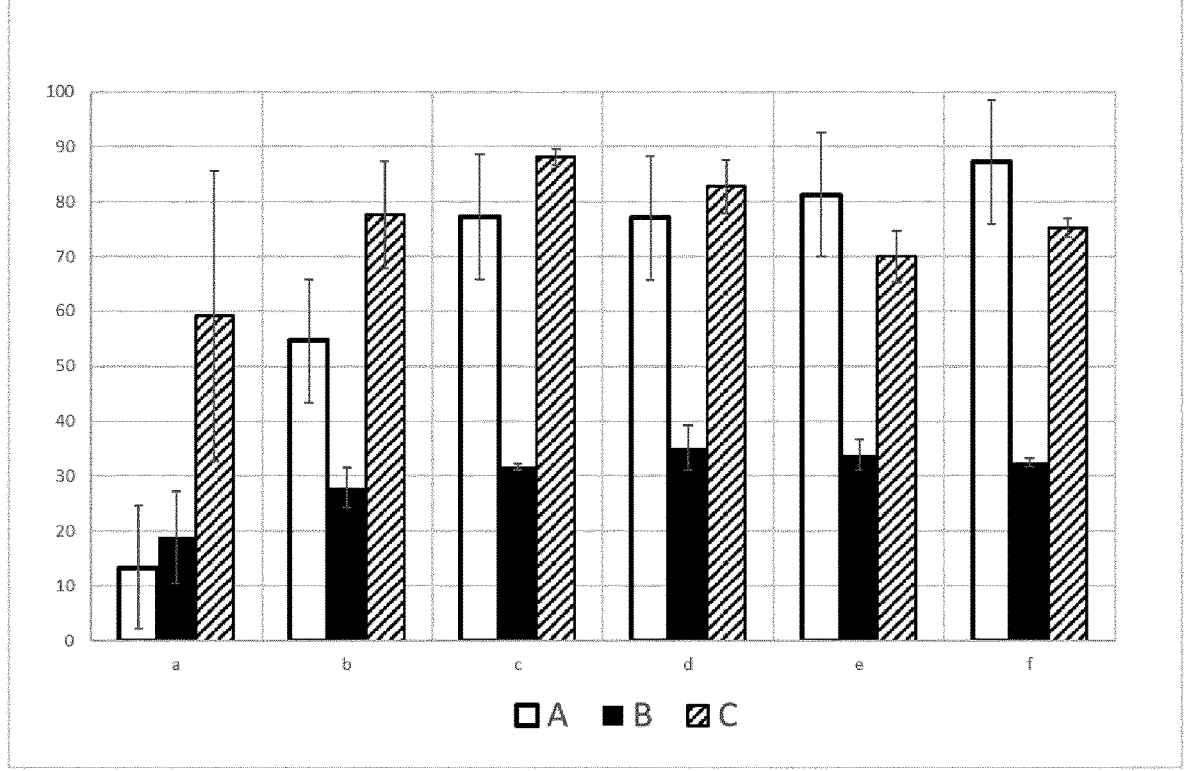

FIG. 2: Filtrating excess metabolic water away by using porous membrane filter under cell retention conditions and regulating the pH under ammonium reduction conditions (preliminary experimentation). Cell retention experiment 1. Phases/conditions (horizontal coordinate): a.: cell growth. b.: cell retention filter test. c.: production without cell retention. d.: production with cell retention. e.: production with cell retention and ammonia reduction. f.: production with cell retention without ammonia feeding. Vertical coordinate Means and standard deviation. A: OD610. B: VVD [L/L/d]. C: Conversion [%].

Figure 3:
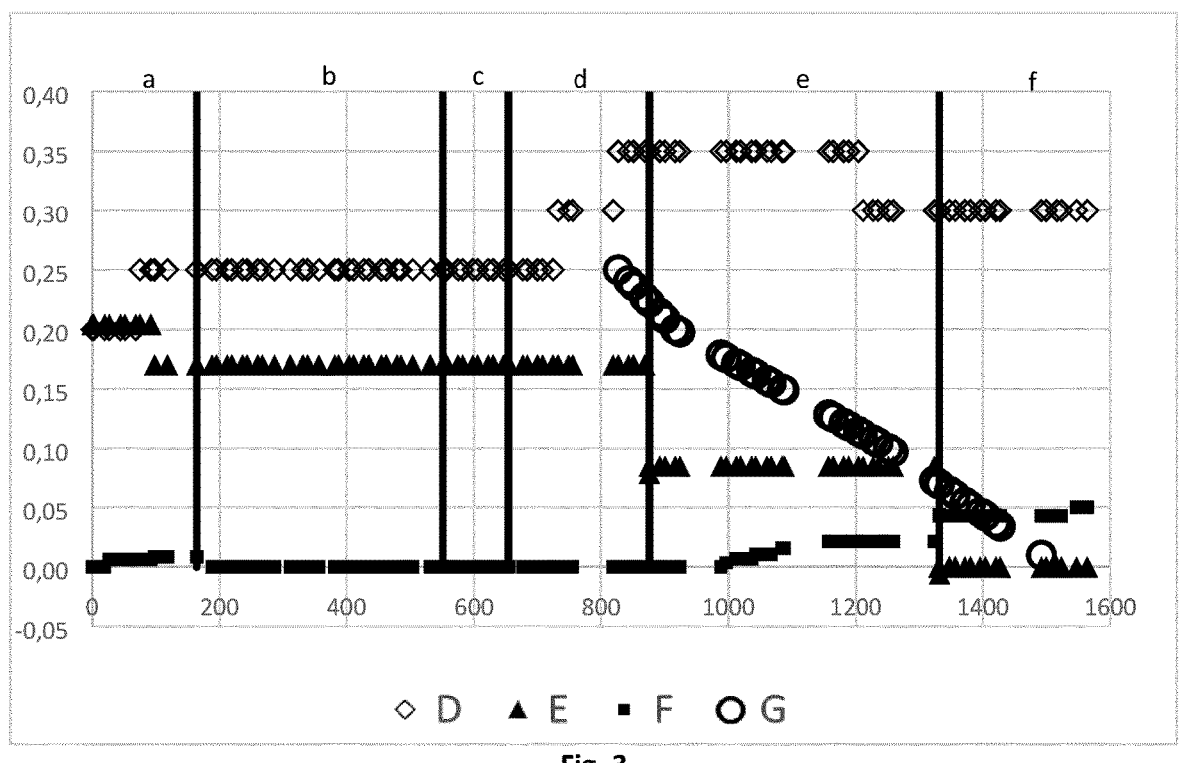

FIG. 3: Filtrating excess metabolic water away by using porous membrane filter under cell retention conditions and regulating the pH under ammonium reduction conditions (preliminary experimentation). Cell retention experiment 1. Horizontal coordinate: run time [h]. Vertical coordinate: D: CO2 flow [L/min]. E: feeding NH3 [g/l/d]. F: feeding NaOH [M/l/d]. G: NH4+ concentration supernatant [g/L]. Phases/conditions: a: cell growth. b: cell retention filter test. c: production without cell retention. d: production under cell retention. e: production under cell retention and ammonia reduction. f: production under cell retention without ammonia feeding.

Figure 4:
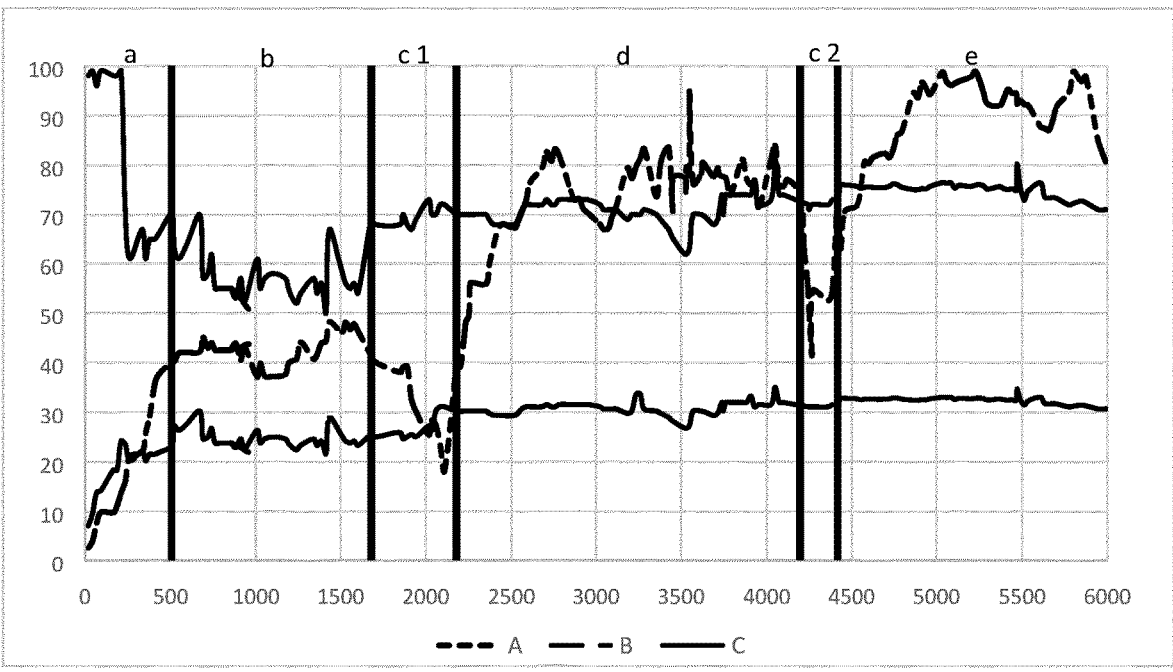

FIG. 4: Filtrating excess metabolic water away under cell retention conditions by using porous membrane filter with no need to regulate an initial set pH value under ammonium reduction conditions (cell retention experiment 2). Horizontal coordinate: run time [h]. Vertical coordinate: A: OD610. B: WD [L/L/d]. C: Conversion [%]. Phases/condition: a: cell growth. b: methane production under no cell retention. c: transition 1 and 2. d: methane production under cell retention. e: methane production under cell retention and ammonia reduction.

Figure 5:
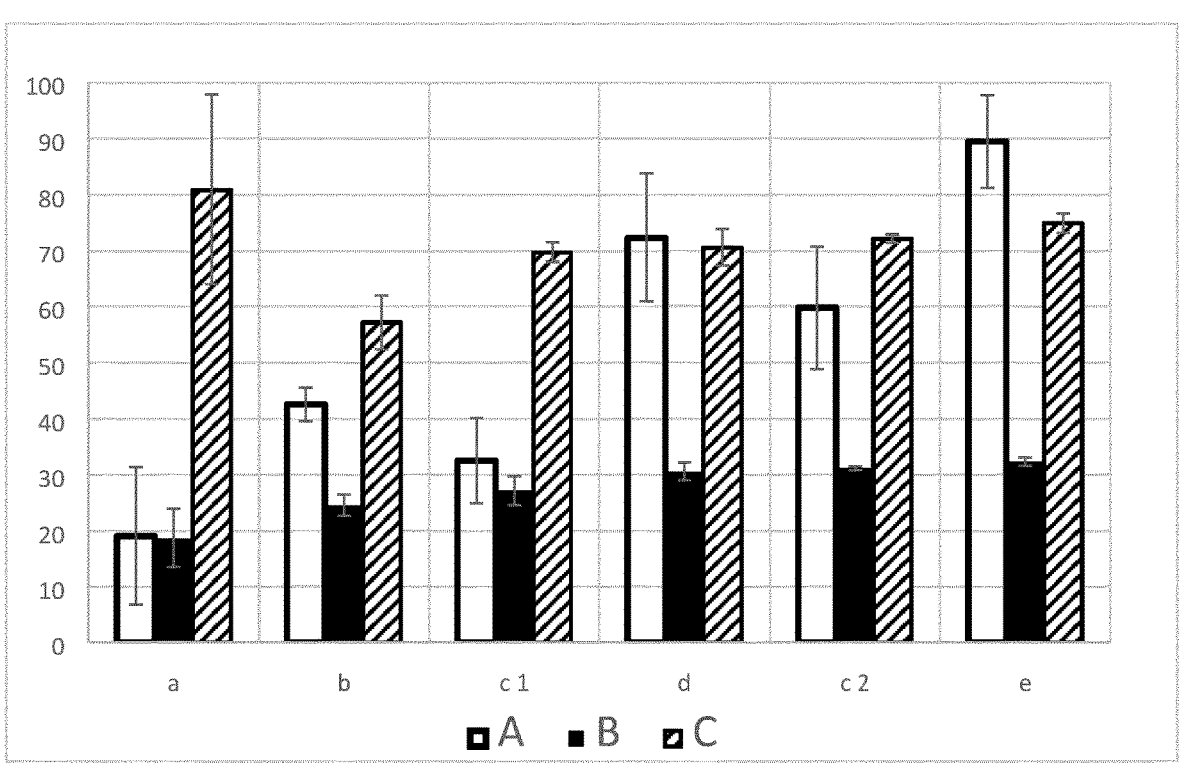

FIG. 5: Filtrating excess metabolic water away under cell retention conditions by using porous membrane filter with no need to regulate an initial set pH value under ammonium reduction conditions (cell retention experiment 2). Phases/conditions (horizontal coordinate): a: cell growth. b: methane production without cell retention. c: transition 1 and 2. d: methane production under cell retention. e: methane production under cell retention and ammonia reduction. Vertical coordinate Means and standard deviation: A: $OD_{610.}$ B: VVD [L/L/d]. C: Conversion [%].

Figure 6:
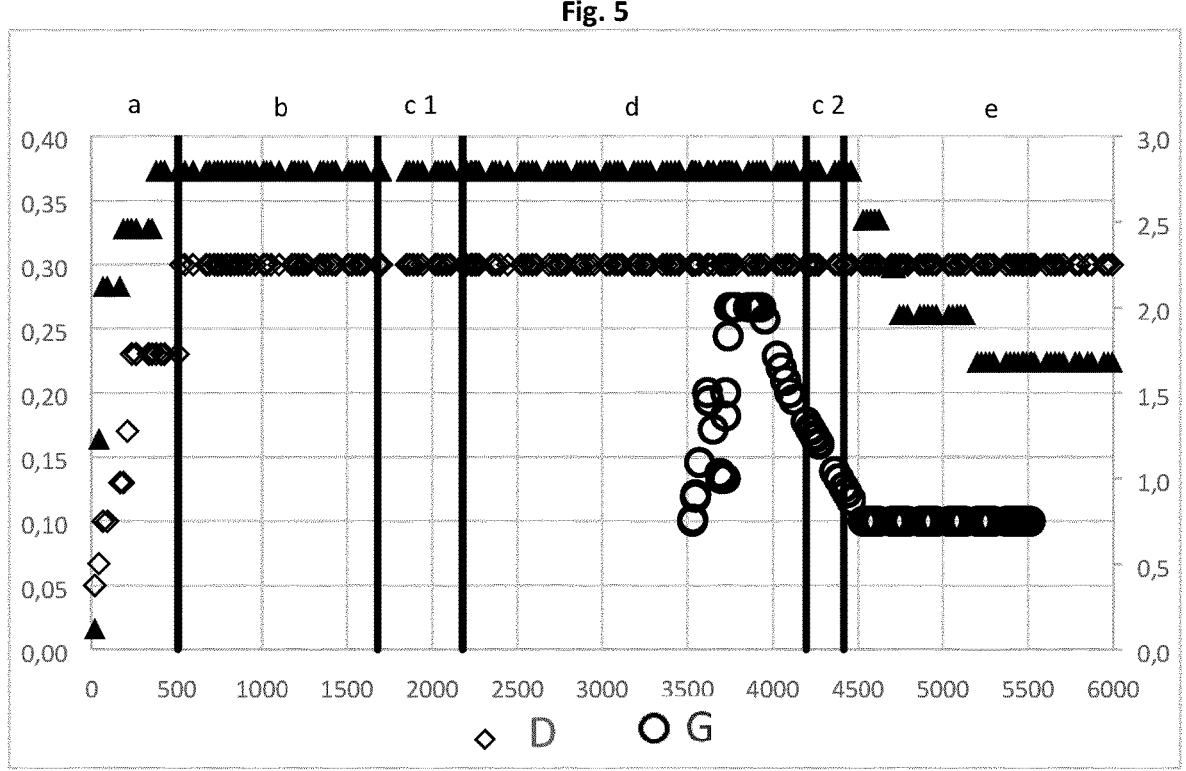

FIG. 6: Filtrating excess metabolic water away under cell retention conditions by using porous membrane filter with no need to regulate an initial set pH value under ammonium reduction conditions (cell retention experiment 2). Horizontal coordinate: run time [h]. left vertical coordinate: D: $CO_2$ flow [L/min]. E: feeding NH3 [g/L/d]. right vertical coordinate: G: NH4+ concentration supernatant [g/L]. Phases/ conditions: a: cell growth. b: methane production without cell retention. c: transition 1 and 2. d: methane production under cell retention. e: methane production under cell retention and ammonia reduction.

Figure 7:
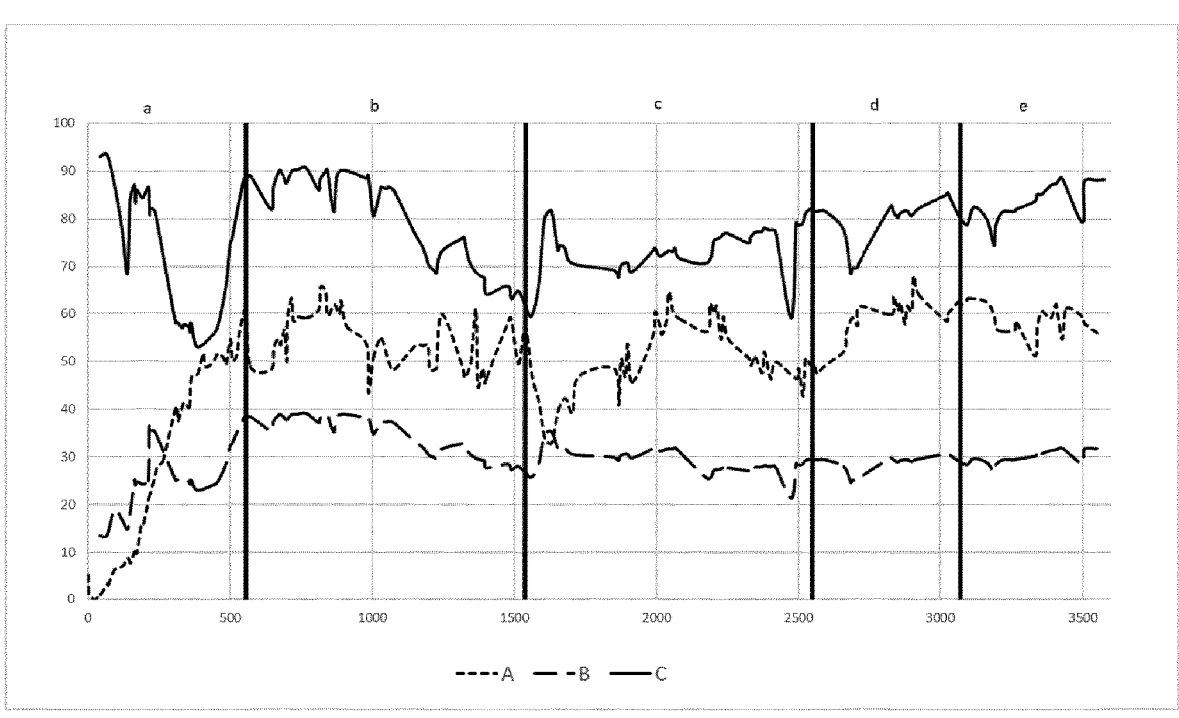

FIG. 7: Methane production under cell retention conditions and culture medium component recycling using filters to remove excess metabolic water away (cell retention experiment 3). Horizontal coordinate: run time [h]. Vertical coordinate: A: OD610. B: VVD [L/L/d]. C: Conversion [%]. Phases/conditions: a. cell growth under cell retention. b. methane production under cell retention. c. methane production under cell retention and nutrient recovery. d. methane production under cell retention and ammonia reduction. e. methane production under cell retention without ammonia feeding.

Figure 8:
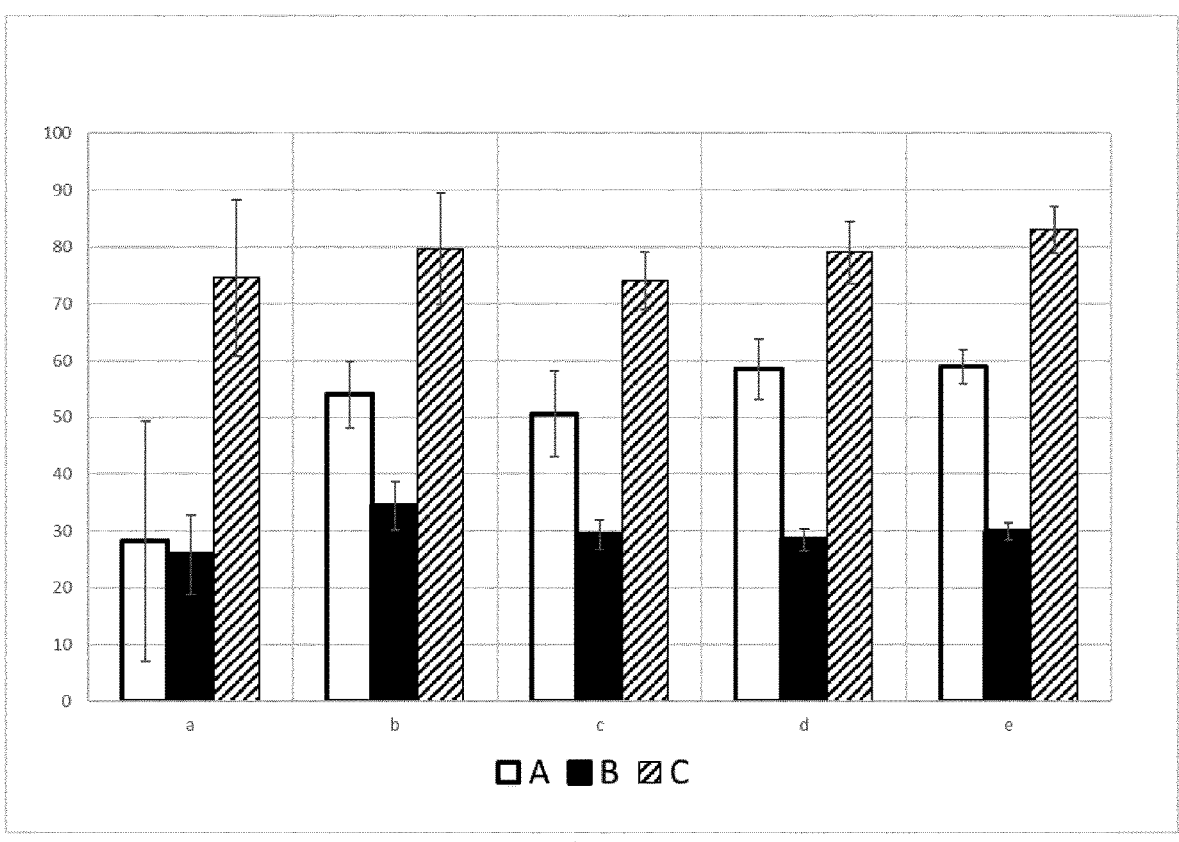

FIG. 8: Methane production under cell retention conditions and culture medium component recycling using filters to remove excess metabolic water away (cell retention experiment 3). Phases/conditions (horizontal coordinate): a. cell growth under cell retention. b. methane production under cell retention. c. methane production under cell retention and nutrient recovery. d. methane production under cell retention and ammonia reduction. e. methane production under cell retention without ammonia feeding. Vertical coordinate Means and standard deviation. A: OD610. B: WD [L/L/d]. C: Conversion [%].

Figure 9:
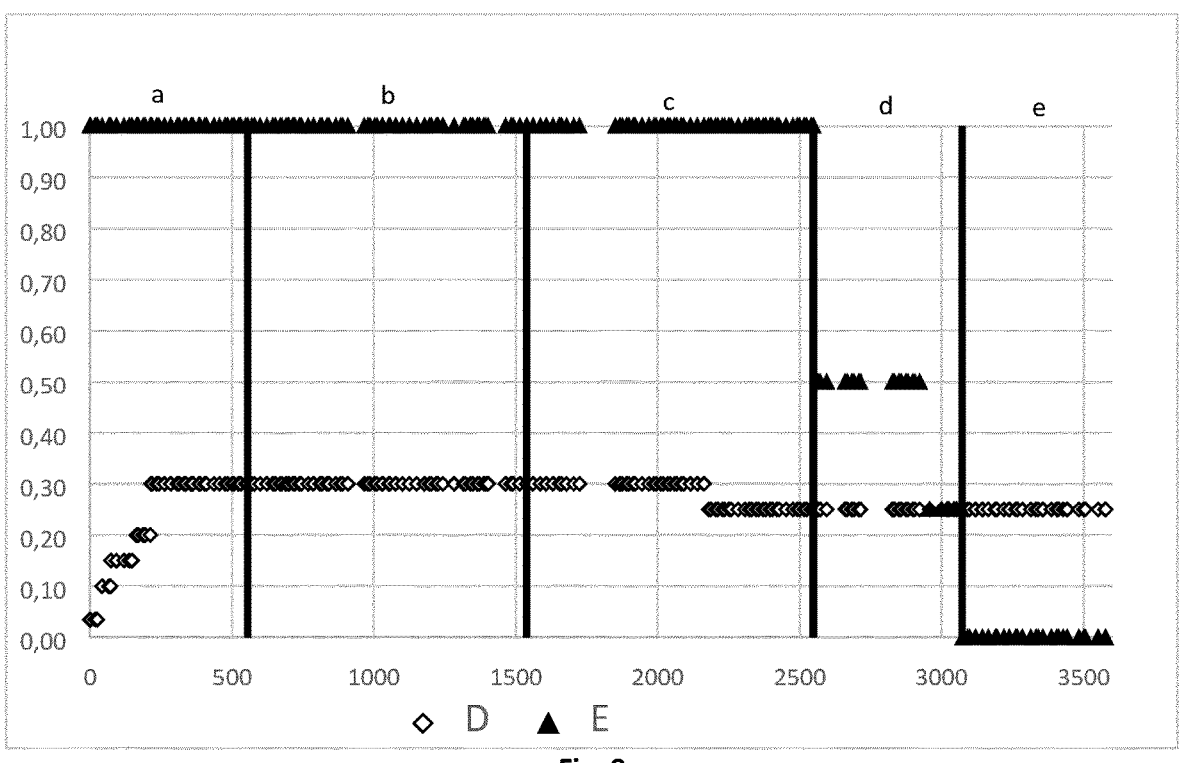

FIG. 9: Methane production under cell retention conditions and culture medium component recycling using filters to remove excess metabolic water away (cell retention experiment 3). Horizontal coordinate: run time [h]. Vertical coordinate: D: CO2 flow [L/min]. E: NH3 feeding related to standard feeding [%/100] showing the reduction to 50%, 25% and 0% of standard feeding. Phases/conditions: a. cell growth under cell retention. b. methane production under cell retention. c. methane production under cell retention and nutrient recovery. d. methane production under cell retention and ammonia reduction. e. methane production under cell retention without ammonia feeding.

Figure 10:
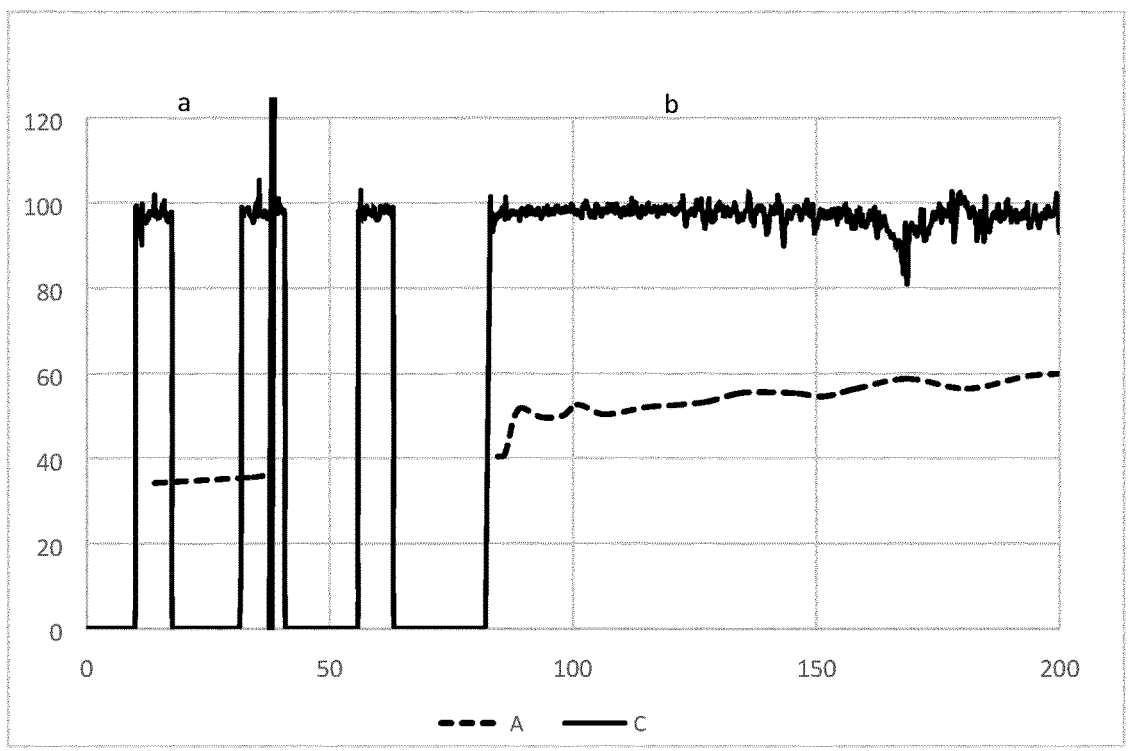

FIG. 10: Filtrating excess metabolic water away under cell retention conditions by using reverse osmosis filters (cell retention experiment 4). Horizontal coordinate: run time [h]. Vertical coordinate: A: OD610. C: Conversion [%]. Phases/conditions: a: methane production without cell retention and medium recovery. b: methane production under cell retention and medium recovery.

Figure 11:
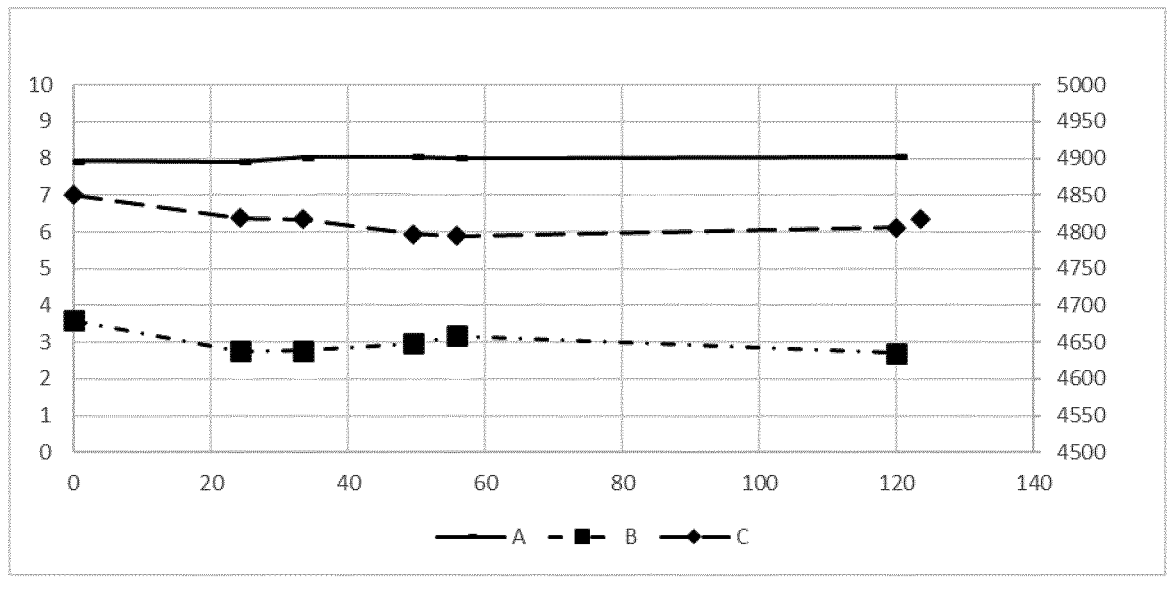

FIG. 11: Removal of excess metabolic water by evaporation under cell retention conditions (cell retention experiment 5). Operation of an industrial scale reactor containing *Methanothermobacter thermautrophicus* UC 120910 (ECH0100) over a 5-day period. Horizontal coordinate: run time [h]. Vertical coordinate left: (A.) pH, (B.) OD, Vertical coordinate right: (C.) reactor mass (kg). Reactor mass is the weight of the liquid medium and the biomass in the reactor, which was determined with a scale that was tared for the weight of the reactor itself.

Figure 12:
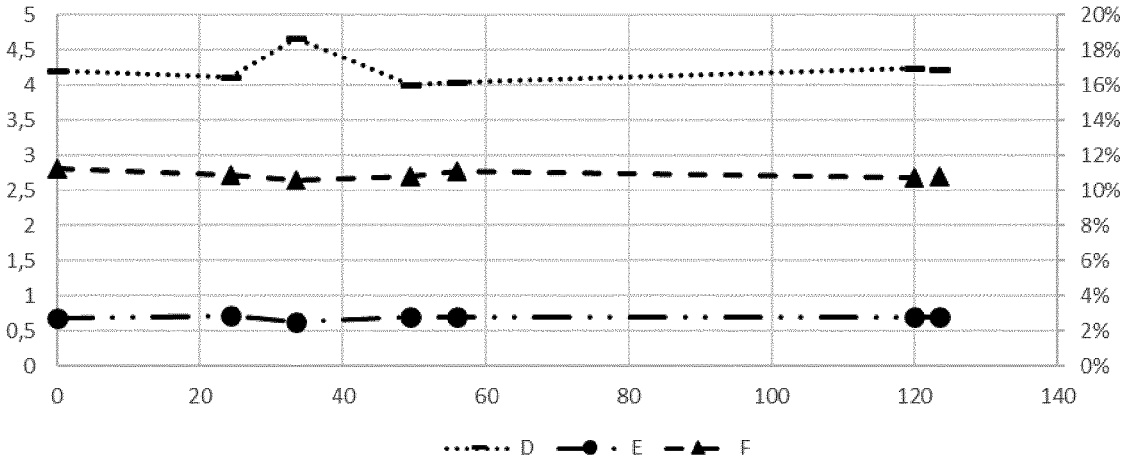

FIG. 12: Removal of excess metabolic water by evaporation under cell retention conditions (cell retention experiment 5). Operation of an industrial scale reactor containing *Methanothermobacter thermautrophicus* UC 120910 (ECH0100) over a 5-day period. Horizontal coordinate: run time [h]. Vertical coordinate left: (D.): Ratio of H2: CO2 in the inlet gas of the reactor, (E.) the flow rate of biogas (Nm3/h) into the reactor. Vertical coordinate right: (F.) the percentage of CO2 in the product gas, the gas flowing from the outlet of the reactor.

Figure 13:
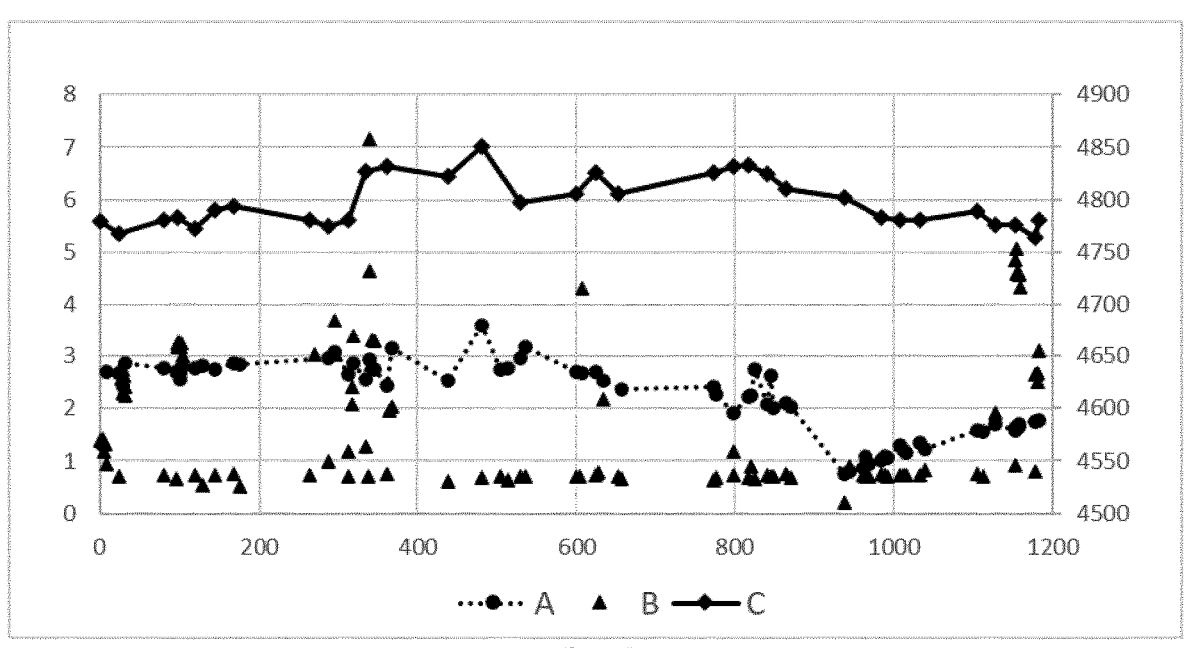

FIG. 13: Removal of excess metabolic water by evaporation under cell retention conditions (cell retention experiment 5). Operation of an industrial scale reactor containing *Methanothermobacter thermautrophicus* UC 120910 (ECH0100) over a 5-day period. The graph shows (A.) reactor mass (kg), (B.) OD, (C.) the flow rate of biogas (Nm3/h) into the reactor. Reactor mass is the weight of the liquid medium and the biomass in the reactor, which was determined with a scale that was tared for the weight of the reactor itself.

FIG. 14: Reactor set up for removal of excess metabolic water by using a porous filter within the bioreactor cell culture medium (e.g., cell retention experiments 1 and 2). Experimental set-up. a: ceramic filter. b: reactor. c: metabolic water. A laboratory scale reactor was supplied with $H_2$, generated by an electrolyser, and $CO_2$. The flow rates of hydrogen and carbon dioxide were adjusted to a 4:1 ratio. The temperature of the culture was 62.5° C. and the methanation reaction occurred at atmospheric pressure. The produced metabolic water of the reactor was removed with a ceramic filter which was located inside the reactor. With this membrane the complete metabolic water containing dissolved nutrients was removed, only cells were retained in the reactor. To balance the loss of nutrients, media stock solutions were dosed according to the discharge volume.

FIG. 15: Reactor set up for removal of excess metabolic water by using a reverse osmosis filter outside of the bioreactor (cell retention experiment 4). Experimental set-up. a: reactor. b: metabolic water. c: R/O membrane. d: cells/nutrients. An industrial scale reactor was supplied with $H_2$, generated by an electrolyser, and $CO_2$, a byproduct of biogas purification. The flow rates of hydrogen and carbon dioxide were adjusted to a 4.1:1 ratio. The temperature of the culture was 62.5° C. and the methanation reaction occurred at 10 bar. Biocatalyst liquid was removed from the reactor and passed through a R/O membrane to remove the produced metabolic water. The cells and most of the dissolved nutrients were returned to the reactor after passing by the membrane.

Figure 16:
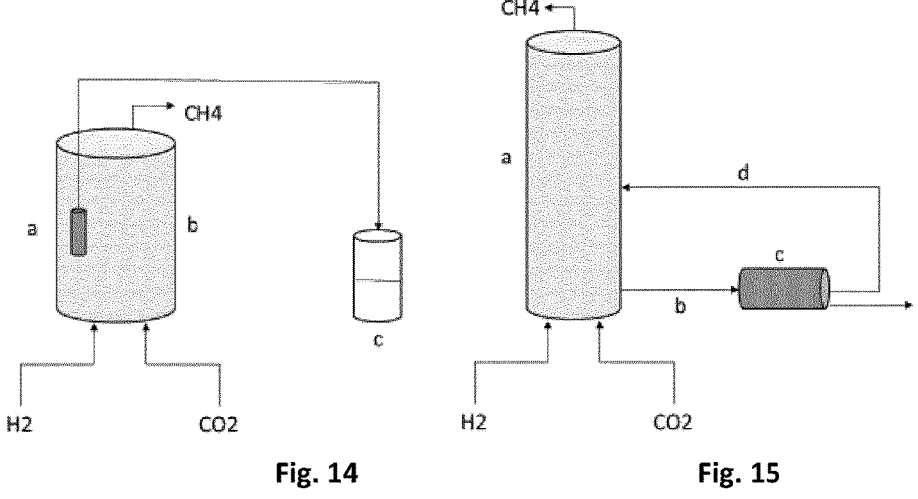

FIG. 16: Reactor set up for removal of excess metabolic water by using evaporation (cell retention experiment 5). Experimental set-up. a: reactor. b: water vapor. c: condenser. d: metabolic water.

FIG. 17. A: photo of the cell morphology of the Methanothermobacter thermautrophicus UC 120910 (ECH0100) of experiment 1 from a qualitative control sample derived from cells which were cultured in a growth-phase under no cell retention conditions. As can be seen longer cells predominated.

B: photo of the cell morphology of the Methanothermobacter thermautrophicus UC 120910 (ECH0100) of experiment 1 from a sample grown under cell retention conditions. As can be seen short straight cells were predominated.

EXAMPLES

The following examples illustrate viable ways of carrying out the described method as intended, without the intent of limiting the invention to said examples.

Example 1: Cell-Retention Experiment 1

The inventors of the present invention have set themselves the task to provide a method to convert $H_2$ and $CO_2$ into methane by methanogenic microorganisms in a scalable, reliable and continuous production process for methane enriched gas compositions.

Therefore, the inventors have tested a new approach to culture methanogenic microorganisms, namely by applying cell retention conditions. One method to retain the methanogenic microorganisms was tested by the inventors by means of filtration to remove excess formed metabolic water during the methanation production phase. The concept was realized in the form of a ceramic filter unit suitable for microfiltration, which was submerged into the cell culture suspension close to the surface of the cell culture medium inside the reactor (reduced outline of experimental set-up depicted in FIG. 14). Ceramic filters were supplied by Katadyn Deutschland GmbH and Guangzhou PUREEASY Hi-Tech CO., LTD, with pore sizes of 0.3 μm and 0.1 μm, respectively. Filter housings were constructed from A4 stainless steel parts. By using microfiltration, all cells were kept inside the reactor (cell retention).

Moreover, the inventors were also interested to test their hypothesis if a given methane productive methanogenic microorganism population under cell retention conditions could still be stably maintained over time under conditions where the supply of the nitrogen source is reduced or even completely stopped.

The experiment was conducted in a 10 L bioreactor and covered within 1,600 h total running the following different process conditions/phases:
a. cell growth.
b. filter testing under cell retention.
c. methane production without (under no) cell retention.
d. methane production under cell retention.
e. methane production under cell retention and ammonia reduction.
f. methane production under cell retention without ammonia supply.

The experimental set-up is depicted in FIG. 14 in simplified form. The used instruments and information for the measurement of parameters for experiment 1 are shown in Table 1.

TABLE 1

| Used instruments and information for the measurement of parameters for experiment 1. | | |
| --- | --- | --- |
| Parameter | | Instruments and description |
| Sampling | Cell-suspension: | 60 ml syringe at sampling-port on top of the reactor |
| | Metabolic water: | 60 ml syringe at valve of metabolic water discharge (discharge-port to the filter) |
| Removal of metabolic water | Normal operation: | Manually at sampling-port (with vacuum pump) |
| | Cell-retention: | Continuously with pumps |
| $OD_{610nm}$ | Photometer (MD610-WTW/ Photoflex-Lovibond) | Optical density at 610 nm |
| Conversion/ VVD | Micro Gas Chromatograph (Agilent Technologys) Gas bag | Product gas was collected in gas bags and attached to the microGC inlet. Measurement of gas composition using calibration curves; calculation of $CO_2$ conversion (based on determined $H_2$ and $CH_4$ concentrations) and VVD (volume of methane/reactor volume/day) |
| Ammonium | Quantofix Ammonium | Cell suspension was sampled from the reactor and spun down to separate the cells from the liquid. Ammonia was measured in the liquid using test strips according to the manufacturer's instructions. 10-400 mg/l $NH_4^+$ (compare undiluted and 1:10 diluted fresh supernatant). |

The results of the experiment 1 are depicted in FIGS. 1, 2 and 3. The duration of the growth phase (phase index a)

was 165 h when the density of the culture increased up to $OD_{610}$ 30 followed by further increase to $OD_{610}$ 80 during a 387 h lasting period of testing different filter materials for the cell retention (phase index b) using a filter with a pore diameter of 0.1 μm or one with a pore diameter of 0.3 μm. After chosen a filter with a pore diameter of 0.3 μm for all of the further cell retention phases, the $OD_{610}$ reaching a stationary phase, wherein cell density remained very stable during methane production phase without cell retention (duration: 97 h, phase index c, see also in FIGS. 1 and 2), cell retention condition (duration: 221 h, phase index d), ammonia reduction condition (duration: 440 h, phase index e) and the phase of no ammonia dosing (duration: 216 h, phase index f). Thus, indicating that the cell density advantageously remained quite unaffected after applying ammonium reduction conditions or even after a complete stop of additional ammonium supply.

In the cell retention filter test phase two filters (0.1 and 0.3 μm) were tested and qualitatively compared. For the testing of different filters, two additional ports were used and tested simultaneously next to each other to compare. One was used for the 0.1 μm filter and another one for a 0.3 μm filter. They were submerged into the cell-suspension between the Rushton impellers. The procedure was a manual discharge of the supernatant over both filters with a vacuum pump. For the comparison the flow, OD and a microscope (40×) were qualitatively used.

The flow of the 0.1 μm filter was slow and it needed more than the double time to reach the same volume with the help of the vacuum pump. With both filters, the optical densities and qualitative comparison of the number of cells in the filtrate were the same. The reason of the lower flow of the 0.1 μm filter could also lie in the smaller surface. At longer runtime of the vacuum pump, a general decrease in the flow was also noted. Because of the higher flow, the filter with a pore size of 0.3 μm was used in the following experiments of cell-retention.

To verify the unproblematic switch between the discharge of only supernatant (cell-retention) and discharge of cell-suspension (production phase without cell retention, FIGS. 1, 2 and 3, phase c) there was a short switch back to normal mode performed for one week. The results show that with continuous ammonia-dosing, the cells start to reproduce again, and no washout takes place. The discharge was done manually once per day.

The methane production rate is a measure of process kinetics and often indicated by the volume of methane per volume of cell-suspension and per day (abbreviated as WD in the following). As can be seen in FIGS. 1 and 2 the average $CO_2$ conversion rate and consequently VVD were lowest and standard deviations were highest during the initial growth phase (60% or 8.2 L/L/d respectively) due to the process-related increase of the flow from 0.75 L H2 to 0.945 L H2 per minute during the start-up. The filter testing period is characterized by changes and adaptations in the experimental setup resulting in a drop with major fluctuations both of the conversion rate and the VVD. During these fewer stable conditions, mean conversion rate and VVD remain lower than in the subsequent test phases with expected high standard deviation.

During the production period without cell retention mean (filtration with porous membrane) conversion rate was 88% and was comparable to a rate of 83% during the production period under cell retention conditions. The conversion rates during both ammonia reduction (70%) and no ammonia dosing (75%) under cell retention conditions were smaller than the ones in the production period without cell retention and the production period with cell retention. Nevertheless, advantageously and surprisingly the conversion rate was still quite high under such reduced or stopped ammonium supply conditions when simultaneously culturing the cells under cell retention conditions arguing for an overall high efficiency of the experimental set-up of the applied system.

The VVD dependent on the $CO_2$ conversion followed the trend of the conversion rate of above. However, within error limits during the production period without cell retention the VVD with on average 31.7 L/L/d was statistically not significant different towards the VVD during the cell retention phases (VVD=35 L/L/d), the cell retention with reduced ammonia (VVD=34,1 L/L/d) and the cell retention without ammonia feeding (VVD=32,4 L/L/day; cf. FIGS. 1 and 2, graph/bar "B") further indicating an overall high efficiency of the experimental set-up of the applied system under cell retention conditions only or under cell retention conditions combined with at least the reduction (or complete stopping) of the ammonium supply.

During the cell retention phase the flow was increased twice (first: 1.2 L $H_2$/min, second: 1.47 L $H_2$/min) which is recognizable by two decreases of the conversion. At the first increase of the flow there was a recovery of the conversion to the level before (90%) but the second increase lead to a stable phase with a lower conversion (78%). The last flow-increase with a lower conversion and no increase of the WD compared to the flow-increase before, was a sign that this was already a too high flow for the reactor: the highest gas feed input could not be completely processed by the bio-catalyst due to limited agitator performance in the reactor. Therefore, it was ramped down to 1.2 L H2/0.3 L $CO_2$.

Next the inventors were interested to test their hypothesis that the cells tolerate lower ammonia dosing once a stable cell population is established. Ammonia is required for growth and since the cells are being retained ammonia should not be required any more. To test this correlation and to verify the previous experiments, a solution with the half ammonia concentration (1.2 M NH4OH) was used for dosing. To control the pH sodium hydroxide 3 molar was added with a pump.

The concentration of ammonia during the decreasing phases shows the dropping NH4'-concentration from 250 mg NH4'/L initially to 100 mg NH4'/L at the end of the period with reduced ammonia feeding and 10 mg NH4'/L at the end of the experiment. The pH stabilisation was conducted by addition of NaOH.

An extremely stable process overall production periods (no cell retention, cell retention, and cell retention with reduced and without ammonia feeding) with only minor fluctuations, recognizable by low standard deviations, are noticeable.

Thus, the inventors of the present invention have surprisingly found, that by cultivating methanogenic microorganisms under cell retention conditions according to the present invention it is possible (in this example subsequent a growth phase) to tremendously reduce or even completely stop the supply of the nitrogen source in the methane production phase as still a high and quite stabilized methanation rate was observed in theses phases compared with phases with full ammonium supply over time while maintaining cell culture number (cf. FIGS. 1, 2 and 3, especially phase indices e and f compared with d (and additionally c)).

A surprising effect was noticed by the inventors when the cells were cultivated under cell retention conditions. According to the experimentation the inventors performed the test methanogenic microorganism Methanothermobacter thermautrophicus UC 120910 (ECH0100) showed a remarkably change in cell morphology (cells became significant shorter) during the various phases under cell retention conditions towards comparable conditions under no-cell retention conditions (see FIGS. 17 A, B), which could be generally observed in the various cell retention experiments performed.

After reduction or stopping of $NH_4OH$ supply to the culture medium the pH stabilisation was conducted by addition of NaOH.

However, the inventors noticed that the adding of base (NaOH) detrimentally lead to a quite unstable pH in the beginning, which needed some time to be stabilized to be kept on a given value as before. This unfavorable instable pH effect should be improved by optimizing the experimentation set-up.

To do so and to generally further analyze and improve the former experimental setup and performance further experimentations were performed.

Example 2: Cell Retention Experiment 2

Another long-term method to remove the metabolic water while culturing the methanogenic microorganisms under cell retention conditions was tested.

The experiment 2 was conducted in a 10 L reactor and covered within 6,000 h total running time under the following different process conditions/phases:

a. cell growth.
b. methane production without cell retention.
c. transition 1 and 2
d. methane production under cell retention.
e. methane production under cell retention and ammonia reduction.

The experimental set-up is depicted in FIG. 14 in simplified form. The used instruments and information for the measurement of parameters for experiment 2 are shown in Table 2.

TABLE 2

Used instruments and information for the measurement of parameters for experiment 2.

| Parameter | Instruments and description | |
| --- | --- | --- |
| Sampling | Cell-suspension: | 60 ml syringe at sampling-port on top of the reactor |
| | Metabolic water: | 60 ml syringe at valve of metabolic water discharge (discharge-port to the filter) |
| Removal of the metabolic water | Normal operation: | Manually at sampling-port |
| $OD_{610nm}$ | Cell-retention: | Continuously with pumps |
| | Photometer (MD610-Lovibond) | Optical density at 610 nm |
| Conversion/ VVD | Micro-Gaschromatograph (Agilent Technologys) Gas bag | Measurement of gas composition and calculation of conversion ($CO_2$ or $H_2$ based) and VVD (volume of methane/reactor volume/day) |
| Ammonium | Quantofix Ammonium | Cell suspension was sampled from the reactor and spun down to separate the cells from the liquid. Ammonia was measured in the liquid using test strips according to the manufacturer's instructions. 10-400 mg/l $NH_4^+$ (1:10 diluted fresh supernatant). Performance according to the manufacturer's instructions |

The results of the experiment 2 are depicted in FIGS. 4, 5 and 6. The duration of the growth phase was 500 h when the density of the culture increased up to OD 40. In the following production phase (1,100 h), cell density stayed stable within a range of OD 35-50 (cf. FIGS. 4 and 5).

Before starting the cell retention mode, there was a transition phase (cl: 500 h), in which the density of the culture decreased from OD 40 to OD 18. During this phase, the OD was specifically reduced and then within the transition phase a new cell division and cell growth impulse was initiated. In the cell retention phase (2,000 h), the OD increased to a level above 60 within 200 h and constantly stayed in a range of OD 60-85 during the following 1.800 h. Before starting the ammonia reduction mode, there was another transition phase (c2: 300 h), in which the cell density was specifically reduced to OD 40. In the ammonia reduction mode (1,600 h), cell density increased to a level above OD 80 within 200 h and constantly stayed in a range between OD 80 and 100 during the following 1,400 h.

The average $CO_2$ conversion rate (81%) was highest in the growth phase. The WD (18.7 L/L/d) was lowest and standard deviations were highest during the initial growth phase due to the process-related increase of the flow from 0.05 l to 0.23 l $CO_2$ per minute during the start-up.

However, when applying a methane production phase under no (without) cell retention conditions the $CO_2$ mean conversion rate was detrimentally reduced at levels of 57%. Advantageously, after the methane production phase was performed under cell retention conditions the $CO_2$ mean conversion rate increased during the methane production phase to 71%. Interestingly and surprisingly, when applying a phase under ammonia reduction the $CO_2$ conversion rate increased during the methane production phase to levels of 75%. Consequently, in more detail the VVD was lowest with an average 24.6 L/L/d during the production period without cell retention. The volumetric production rates were significantly higher during the cell retention phase (31.2 L/L/d) and the cell retention with reduced ammonia (32.4 L/L/d). During the cell retention phase and the phase with reduced ammonia, there was no change in flows (1.2 L $H_2$/min, 0.30 L $H_2$/min).

The concentration of ammonia during the decreasing phase shows the dropping $NH4'$-concentration from 373 mg $NH4'$/L/d initially to 224 mg $NH4'$/L/d at the end of the period with reduced ammonia feeding (cf. FIG. 6). The concentration of ammonia in the cell culture medium during the decreasing phase shows the dropping NH4+-concentration from ca. 250-200 mg NH4+/L initially to ca. 100 mg NH4+/L at the end of the period with reduced ammonia feeding at the end of the experiment.

Most interestingly and surprisingly there was no need for pH stabilisation by adding additional amounts of a base like NaOH to compensate for the reduction of $NH_4OH$ supply (as done in cell retention experiment 1 (preliminary experimentation)). In contrast the pH remained stable within minor error tolerances at a given value over the whole further experimentation, i.e. for 800 h until the end of the experiment.

An extremely stable process overall production periods (under no cell retention, under cell retention, and under cell retention with reduced ammonia feeding) with only minor fluctuations, recognizable by low standard deviations, are noticeable.

Example 3: Cell Retention Experiment 3

Experiment 3 was conducted in a 10 L reactor and covered within 3,500 h the following different process conditions/phases:
  a. cell growth under cell retention.
  b. methane production under cell retention.
  c. methane production under cell retention and nutrient recovery.
  d. methane production under cell retention and ammonia reduction.
  e. methane production under cell retention without ammonia supply.

The results of the experiment 3 are depicted in FIGS. 7, 8 and 9. The duration of the growth phase under cell retention conditions was 550 h when the density of the culture increased up to OD 60. In the following continuous methane production phase with cell retention (980 h), cell density was stabilized between OD 50-60.

At the beginning of the nutrient recovery under cell retention condition, which lasted 1,100 h altogether, culture dropped from OD 55 to OD 33 with immediate subsequent regrowth to OD 50 and above. The OD remained stable over the remaining period of the experiment with ammonia reduction (50%, 25%) (550 h) and no ammonia dosing (500 h). Indicating, that the reduction or even the complete stop of the supply of a nitrogen source does not negatively affect the cell density at all.

The differences between these experiment conditions/phases regarding the $CO_2$ conversion rate are not significant, thus indicating in conclusion that the $CO_2$ conversion rate was quite comparable in the various experimental setting of the different phases. In detail, the average $CO_2$ conversion rate (74%) was lowest in the growth phase and in the nutrient recovery phase, medium in the methane production phase with cell retention and the phase of cell retention with reduced ammonia dosing (79%) and highest (83%) when no ammonia was added.

Similarly, the WD was not significant different in the different test conditions after the cell growth phase and remained stable between 26.5 and 34.4 L/L/d. In detail: The VVD (25.9 L/L/d) was lowest and standard deviations were highest during the initial growth phase due to the process-related increase of the flow from 0.035 L to 0.3 L $CO_2$ per minute during the start-up. Similar to the results of the conversation rate and because of some fluctuations.

Example 4: Cell Retention Experiment 4

Experiment 4 was conducted in a 3,500 L bioreactor and covered within 200 h the following different process conditions/phases:
  a. methane production without cell retention and culture medium component recycling.
  b. methane production with cell retention and culture medium component recycling.

The experimental set-up is depicted in FIG. 15. The results of the experiment 4 are depicted in FIG. 10.

For medium recovery a Reverse Osmosis (R/O) membrane/filter unit was used. With this filter/membrane unit metabolic water is removed from the system (permeate) while the cells and minerals which cannot pass the water permeable filter/membrane are accumulated before the filter as retentate and fed back into the reactor with appropriate means, thus allowing to run the reactor system under cell retention conditions.

In the production phase without cell retention and medium recovery (38 h), the OD was stable in a range of OD 34-36. After the production with cell retention and medium recovery was started, the cell density increased to a level above OD 50 within 51 h and constantly stayed in a range between OD 50 and 60 during the following 111 h.

At the beginning of the experiment, the reactor was always switched off after about 8 h. After restarting the reactor, the conversion was always in the same range as before the shutdown. After a running time of 83 h, the reactor was operated continuously without interruptions. The $CO_2$ conversion rate was mainly stable in a range of 90-100%.

The medium recovery and cell retention had no negative effect on the stability of the process, on the contrary the stability of the process remained unaffected under cell retention conditions and medium recycling.

Example 5: Cell Retention Experiment 5

The experimental set-up is depicted in FIG. 16 in a simplified form.
A. Short Term Experiment: Five-Day Experiment
An industrial scale reactor with a filling volume of 4500-5000 L was used. The reactor was supplied with biogas, containing approximately 50% methane and 50% carbon dioxide, from an anaerobic digester. Hydrogen was supplied from a hydrogen tank. The content of $CO_2$ in the biogas was measured using an infrared gas analyzer (IRGA) and the flow rates of biogas and hydrogen were adjusted to achieve a ratio of $H_2$:$CO_2$ that was greater than 4.0. The reactor was placed on an industrial-sized scale. When the reactor was empty, the scale was tared. Thus, the weight measured is only the weight of the contents of the reactor. The temperature of the reactor headspace was 63° C. and the methanation reaction occurred at atmospheric pressure.

During operation, the reactor contents were not drained. The only contents that left the reactor was in the form of water vapor. The gas leaving the outlet of the reactor was saturated with water vapor. This water was condensed and collected from a drain vessel.

The results of the short term (five-days) experiment 5 are depicted in FIGS. 11 and 12.

In the Industrial-scale experiment shown in FIG. 11., the initial reactor mass was 4850 kg. Over the course of the first 50 hours of this experiment, the reactor lost 50 kg of mass through water vapor loss, and the weight of 4800 kg was maintained through the next 70 hours.

Contents were not drained from the bottom of the reactor or elsewhere.
B. Long-Term Results: 50-Day Experiment
Contents were not drained from the reactor during the 50-day experimental period shown in FIG. 12. The reactor was supplied with biogas (50% methane and 50% $CO_2$) and hydrogen at a $H_2$:$CO_2$ ratio greater than 4. The reactor was maintained at 63° C. and atmospheric pressure. The biogas flow and agitator speed were varied during the 50-day period.

The range of reactor mass was from 4750 to 4850 kg. The mass increased when the biogas flow rate was increased (hours 288-365) as a result of increased $CH_4$ and $H_2O$ production. Water vapor released with the outlet (product) gas flow was the only means of removing the $H_2O$ produced by the biocatalyst in the biomethanation reaction.

Thus, showing that removing excess metabolic water via evaporation while running an efficient continuous methanation process is another appropriate option and easy to realize.

The invention claimed is:

1. A method to convert $H_2$ and $CO_2$ into methane or a methane enriched gas composition with a *Methanothermobacter thermoautotrophicus* methanogenic microorganism—in a bioreactor comprising:

(i) culturing the methanogenic microorganism in a liquid culture medium;

(ii) supplying a nitrogen source to the liquid culture medium for cell division and cell growth of the methanogenic microorganism;

(iii) culturing the methanogenic microorganism under cell retention conditions;

(iv) contacting the methanogenic microorganism with at least one feeding gas comprising $CO_2$ and $H_2$;

(v) reducing or stopping the supply of the nitrogen source to the culture medium wherein the supply of the nitrogen source is reduced to a concentration of 0.2 mol/L/day to 0 mol/L/day;

(vi) continuously removing metabolic water in the culture medium from the bioreactor; and (vii) collecting methane or a methane enriched gas composition.

2. The method of claim 1, comprising at least one cycle of culturing the methanogenic microorganism under:

a first phase in a continuous process in a liquid culture medium containing minerals, wherein the supply of at least one mineral to the liquid culture medium is reduced; followed by a second phase, comprising changing the liquid culture medium by adding at least one nutrient which triggers cell division and/or cell growth;

optionally followed by a third phase in a continuous process, wherein the supply of at least one mineral to the liquid culture medium is reduced.

3. The method of claim 2, further comprising at least one cycle of culturing the methanogenic microorganisms under:

a fourth phase under cell retention conditions; followed by a fifth phase, characterized by culturing the cells under no cell retention conditions;

optional followed by a sixth phase under cell retention conditions.

4. The method of claim 1, further comprising:

providing a sulfide source;

maintaining the culture conditions anaerobic or facultatively anaerobic;

optionally stirring the culture; and maintaining the temperatures in a range from 32° C. and 85° C.

5. The method of claim 1, wherein the nitrogen source is selected from ammonium compounds, $NH_4OH$, $NH_4Cl$ or combinations thereof.

6. The method of claim 1, further comprising setting an initial pH value to below pH 9, below pH 8 or at pH 7 and subsequent continuously controlling the pH value.

7. The method of claim 1, wherein the removing of the metabolic water comprises filtrating excess water away from the culture medium and/or comprises the step of evaporating excess water from the culture medium.

8. The method of claim 7, wherein the filtrating of excess water away from the culture medium is performed by reverse osmosis using at least one semipermeable membrane for water in contact with the culture medium.

9. The method of claim 7, wherein the filtrating of excess water away comprises:

removing fractions of cell-free culture medium from the bioreactor by filtration through at least one porous membrane in contact with the culture medium; and optionally, subsequently concentrating the minerals from the removed culture medium; and optionally, at least partially recycling the concentrated minerals back to the bioreactor.

10. The method of claim 2, further comprising:

controlling and optionally regulating at least one of the minerals in the culture medium by additional adding of minerals.

11. The method of claim 1, wherein during the culturing at least 60% of the overall methanogenic microorganism in the bioreactor have a ratio of length to width of 5:1 to 3:1.

12. The method of claim 11, wherein more than 80% of the overall methanogenic microorganisms in the bioreactor have a ratio of length to width of from 4:1 to 3:1.

13. The method of claim 12, wherein the ratio is 3:1.

14. The method of claim 1, wherein prior to reducing or stopping the supply of the nitrogen source the culturing of the methanogenic organisms comprises controlling and regulating the concentration of a nitrogen source within the culture medium by supplying the nitrogen source to the culture medium in a range of 0.2 mol/L/day to 0.005 mol/L/day, or of 0.02 mol/L/day to 0.01 mol/L/day to enable cell division and cell growth of the methanogenic microorganisms; and culturing the methanogenic microorganisms up to a density in the culture medium measured as $OD_{610}$ being at least 1, 9 up to 200, at least 20 up to 120, or at least 60 up to 100 and corresponding to a dry weight of the microorganisms in the culture of at least 0.5 g/L and up to 50 g/L or at least 6.5 g/L and up to 31.3 g/L or at least 18.3 g/L and up to 26.1 g/L respectively.

15. The method of claim 4, wherein the sulfide source is in the form of sodium sulfide ($Na_2S$) or hydrogen sulfide ($H_2S$).

16. The method of claim 9, wherein the porous membrane has the pore size of 0.4 to 0.1 µm.

17. The method of claim 16, wherein the porous membrane has the pore size of 0.3 µm.

18. The method of claim 9, wherein concentrating the minerals is performed by nanofiltration, ultrafiltration and/or distillation, one or more times.

* * * * *